US012797613B2

(12) United States Patent
Lee et al.

(10) Patent No.: US 12,797,613 B2
(45) Date of Patent: Nov. 17, 2026

(54) LOW-POWER STRETCHABLE NEUROMORPHIC NERVE DEVICE WITH PROPRIOCEPTIVE FEEDBACK

(71) Applicants: SEOUL NATIONAL UNIVERSITY R&DB FOUNDATION, Seoul (KR); The Board of Trustees of the Leland Stanford Junior University, Stanford, CA (US)

(72) Inventors: Tae-Woo Lee, Seoul (KR); Yeongjun Lee, Seongnam-si (KR); Zhenan Bao, Stanford, CA (US); Yuxin Liu, Singapore (SG)

(73) Assignees: SEOUL NATIONAL UNIVERSITY R&DB FOUNDATION, Seoul (KR); THE BOARD OF TRUSTEES THE LELAND STANFORD JUNIOR UNIVERSITY, Stanford, CA (US)

(*) Notice: Subject to any disclaimer, the term of this patent is extended or adjusted under 35 U.S.C. 154(b) by 775 days.

(21) Appl. No.: 18/303,958

(22) Filed: Apr. 20, 2023

(65) Prior Publication Data

US 2024/0350800 A1 Oct. 24, 2024

(51) Int. Cl.

| | |
|---|---|
| ***G06N 20/00*** | (2019.01) |
| ***A61N 1/36*** | (2006.01) |
| ***G06N 3/06*** | (2006.01) |
| ***G06N 3/063*** | (2023.01) |
| ***H10D 84/00*** | (2025.01) |

(52) U.S. Cl.
CPC ......... *A61N 1/36003* (2013.01); *G06N 3/061* (2013.01); *G06N 3/063* (2013.01); *H10D 84/00* (2025.01)

(58) Field of Classification Search
CPC .... A61N 1/36003; G06N 3/061; G06N 3/063; G06N 3/049; G06N 3/065; H10D 84/00
See application file for complete search history.

(56) References Cited

U.S. PATENT DOCUMENTS

| | | | | |
|---|---|---|---|---|
| 9,987,167 B2 * | 6/2018 | Lorach | ................. | G09B 21/008 |
| 2019/0311255 A1 * | 10/2019 | Wang | .................. | G06F 12/0238 |

FOREIGN PATENT DOCUMENTS

| | | | | |
|---|---|---|---|---|
| CA | 2850434 A1 * | 4/2013 | ......... | A61N 1/36135 |
| CN | 103608069 A * | 2/2014 | ............. | A61B 5/296 |
| CN | 113607628 B * | 2/2023 | ............... | G06N 3/08 |
| KR | 10-2019-0136402 A | 12/2019 | | |

(Continued)

OTHER PUBLICATIONS

Yeongjun Lee et al., "A low-power stretchable neuromorphic nerve with proprioceptive feedback", Nature Biomedical Engineering, 2022, 45 pages, [https://doi.org/10.1038/s41551-022-00918-x].

(Continued)

*Primary Examiner* — Hassan Mrabi
(74) *Attorney, Agent, or Firm* — Sughrue Mion, PLLC

(57) ABSTRACT

Disclosed herein are a neuromorphic nerve device including an artificial proprioceptor device and an artificial synapse, and a neuromorphic prosthetic device using the same. The neuromorphic nerve device in accordance with the present disclosure is simple in structure, is drivable with low power, and excellent in stretchability, so that a robot made of a soft material similar to a human or an animal can be made, and a neuromorphic prosthetic device that is comfortable for a user to wear can be made possible.

23 Claims, 12 Drawing Sheets

(56) References Cited

FOREIGN PATENT DOCUMENTS

| | | | | | |
|---|---|---|---|---|---|
| KR | 10-2019-0136419 | A | | 12/2019 | |
| WO | WO-2015061453 | A1 | * | 4/2015 | ......... A61N 1/36003 |

OTHER PUBLICATIONS

Lorenzo Vannucci et al., "Proprioceptive Feedback through a Neuromorphic Muscle Spindle Model," Frontiers in Neuroscience, Jun. 14, 2017, vol. 11, No. 341, pp. 1-13 (15 pages total).

Chenghao Chen et al., "Functional architecture of neural circuits for leg proprioception in *Drosophila*," Current Biology, Dec. 6, 2021, vol. 31, No. 23, pp. 5163-5175.e1-e7 (23 pages total).

Fuqin Sun et al., "An artificial neuromorphic somatosensory system with spatio-temporal tactile perception and feedback functions," NPJ Flexible Electronics, Aug. 13, 2022, vol. 6, No. 72, pp. 1-8 (10 pages total).

Egidio Falotico et al., "Connecting Artificial Brains to Robots in a Comprehensive Simulation Framework: The Neurorobotics Platform," Frontiers in Neurorobotics, Jan. 25, 2017, vol. 11, No. 2, pp. 1-23 (25 pages total).

International Search Report and Written Opinion issued Jan. 12, 2024 in Application No. PCT/KR2023/011995.

* cited by examiner

LOW-POWER STRETCHABLE NEUROMORPHIC NERVE DEVICE WITH PROPRIOCEPTIVE FEEDBACK

BACKGROUND

The present disclosure relates to a neuromorphic nerve device, and more particularly, to a low-power stretchable neuromorphic nerve device with proprioceptive feedback that functionally replaces damaged nerves to bypass spinal injuries or the damaged nerves, and transmits electrical signals in the form of nerve signals to muscles to restore movement.

Neurological disorders may reduce quality of life and even lead to death. In particular, spinal cord injury (SCI) and motor neuron disease (MND) interfere with transmission of nerve signals from a primary motor cortex to muscles, thereby restricting body movements and significantly degrading a patient's quality of life. Cell therapy and drug treatment aim at complete recovery of damaged nerves, but restoring motor function in a patient with spinal cord injury or motor neuron disease remains a long-standing challenge.

As an alternative, neurorehabilitation devices aimed at restoring a patient's motor function are being developed. Neurorehabilitation devices in the related art use integrated circuits based on the von Neumann architecture, which greatly increase power consumption, have serious heating problems, and do not have plasticity reactions like biological nerves. In addition, for existing stimulation, electric pulses of constant amplitude are used, and thus sudden and rapid contraction of muscles are often induced and muscle contraction force is difficult to predict, which causes inconvenience to users.

In Korean Patent Publication No. 2019-0136419, the present applicant has disclosed an artificial sensory nervous system device using an artificial synaptic device that outputs a post-synaptic signal when a pre-synaptic signal is input. In Korean Patent Publication No. 2019-0136419, it was demonstrated that a post-synaptic current is amplified through a transducer and stimulates the biological efferent nerves and muscles of a cockroach leg and induces movement.

However, there is no neuromorphic nerve device that demonstrates artificial afferent nerves or artificial motor nerves controlling biological motor responses in vertebrates.

SUMMARY

The present disclosure provides a low-power stretchable neuromorphic nerve device capable of controlling body movement by bypassing electrophysiological signal pathways damaged by spinal cord injury or motor neuron disease and redirecting electrophysiological signals.

The present disclosure also provides a neuromorphic nerve device capable of restoring or controlling movement of limbs by receiving nerve signals from the brain using a simple device made up of artificial proprioceptor device and artificial synapses.

The present disclosure also provides a neuromorphic nerve device capable of being driven with low power and being easily manufactured by eliminating limitations such as high power consumption of existing devices that emulate biological synaptic responses.

The present disclosure also provides a neuromorphic nerve device capable of improving natural movement of living organs and comfort of patients by implementing a synaptic potentiation response in which ramping of an output current of an artificial synapse appears using an artificial synapse that emulates a function of a biological synapse, and a stretchable neuromorphic prosthetic device using the same.

In accordance with an exemplary embodiment of the present disclosure, a low-power stretchable neuromorphic nerve device that transmits electrophysiological signals to biological motor organs or, restores or controls motion of the biological motor organs includes an artificial proprioceptor device that emulates an animal's proprioceptor and provides proprioceptive feedback to external stimuli, nerve stimuli, or body movements, and an artificial synapse constituted by a semiconducting structure receiving a signal from the artificial proprioceptor device and outputting, to a living organ, a post-synaptic signal capable of controlling the living organ, here, the artificial proprioceptor device forms a closed feedback loop together with the artificial synapse.

The feedback loop may be a closed negative feedback loop or a closed positive feedback loop.

The animal's proprioceptor may be a muscle spindle or a golgi tendon organ.

The electrophysiological signal may include an electromyogram (EMG), an electrocardiogram (ECG), an electroencephalogram (EEG), an electrooculography (EOG), a receptor potential, and an action potential, and the electrical signal may be changed by detecting a biometric signal by an artificial sensor and changing resistance, current, voltage, and permittivity.

The living organ may include at least one selected from the group consisting of an epithelial cell, a muscle cell, a nerve cell, a fibroblast, a gamete, a brain cell, a bone cell, a cartilage cell, an immunocyte, a secretary cell, a fat cell, a blood cell, a sensory neuron, a merkel cell, a visual cell, an auditory cell, an olfactory cell, a taste cell, a nociceptor, a motor neuron, a muscle fiber, a neuromuscular junction, and a motor unit, but is not limited thereto.

The biological motor organ may include at least one selected from the group consisting of biological muscular fibers, biological motor units (motor neurons and muscle fibers connected thereto), biological motor neurons, and biological neuromuscular junctions.

The artificial proprioceptor device may include one or more sensors selected from the group consisting of a strain sensor for detecting muscle length and force, a pressure sensor, an optical sensor, an image sensor for detecting visual information, an acceleration sensor for detecting balance, and a gyroscope sensor, and a voltage divider configured to adjust an output voltage of the artificial proprioceptor device.

The voltage divider includes one or more resistors and one or more voltage sources.

In accordance with the present disclosure, the strain sensor may include one or more conductive or semiconducting materials selected from the group consisting of carbon nanotubes, carbon nanofibers, carbon black, graphene, two-dimensional (2D) materials (graphene, transition metal dichalcogenide (e.g., $MoS_2$), MXene, graphene oxide, inorganic semiconductor membrane (e.g., Si membrane), or the like), a metal film crack sensor, metal nanowires, metal nanoparticles, conjugated polymers, metal oxide nanoparticles, metal oxide thin films, metal oxide nanowires, and semiconducting nanowires.

The strain sensor may be one or more selected from the group consisting of a piezoresistive strain sensor, a piezoelectric strain sensor, a triboelectric strain sensor, and a capacitive strain sensor that change electrical signals by changing resistance, current, voltage, and permittivity according to strain stimulation or change optical characteristics by changing light transmittance and light absorption.

In accordance with the present disclosure, the low-power stretchable neuromorphic nerve device may use a pressure sensor instead of the strain sensor, and the pressure sensor may include a sensor that detects external light, pressure, touch, friction, sound, vibration, or heat and converts a detected result into an electrical signal.

In accordance with the present disclosure, the artificial synapse may include an active material and one or more selected from the group consisting of a transistor with two or more terminal electrodes, a diode, a resistor, a capacitor, an inductor, an ion pump, and an ion battery structure. The active material may include one or more selected from the group consisting of an organic small molecule semiconductor, an organic polymer semiconductor, a conductive polymer, an insulating polymer, a metal oxide material, a phase change alloy material, a carbon nanomaterial, a nitride material, a two-dimensional layered material, a material having a perovskite structure, a metal nanomaterial, an ionic dielectric material, and a mixture thereof.

A transistor having electrodes of two or more terminals may include a transistor having electrodes of two or more terminals or a transistor having electrodes of three or more terminals, but is not necessarily limited thereto. In more detail, at least one artificial synaptic device may include at least one selected from the group consisting of a transistor having three or more terminal electrodes containing an ionic dielectric material, a flash memory, a magnetic random access memory, a memristor, a resistive random access memory, a magnetoresistive random access memory, and a phase-change memory, but is not limited thereto.

In accordance with the present disclosure, the artificial synapse may include a substrate, and the substrate may be formed of a flexible material, a stretchable material, or a rigid material. The artificial synapse may have a stretchability ranging from 1% to 10,000%. Specifically, the substrate may include a conductor material selected from the group consisting of chromium, aluminum, iron and stainless steel, a semiconductor material selected from the group consisting of germanium, silicon and gallium arsenide, an insulator material selected from the group consisting of glass, sapphire, paper, and plastic film and may include at least one selected from the flexible and stretchable substrate material group consisting of polyimide, polyethylene terephthalate, polyethylene naphthalate, polycarbonate, polyacrylate, polyethersulfone, polypropylene, polydimethylsiloxane, polymethylphenylsiloxane, polydiphenylsiloxane, polysiloxane, polyurethane, polystyrene, a styrene butadiene copolymer, a polystyrene copolymer, and ecoflex, and is not limited thereto. Further, examples of the flexible material may include polyimide, polyethylene terephthalate, polyethylene naphthalate, polycarbonate, polyacrylate, polyethersulfone, and polypropylene, and examples of the material having the stretchability may include polydimethylsiloxane, polymethylphenylsiloxane, polydiphenylsiloxane, polysiloxane, polyurethane, polystyrene, a styrene butadiene copolymer, a polystyrene copolymer, and ecoflex. When thick, the rigid material becomes a rigid substrate material, but when thin, the rigid material becomes a flexible substrate. In addition, although the flexible material is not always stretchable, the stretchable material is also the flexible material.

In accordance with the present disclosure, the artificial synapse may be formed on a flexible and stretchable polymer substrate. A flexible and stretchable artificial synaptic device may be fabricated by using an active material and a conductive electrode material that are stable against mechanical deformation.

For the active material and the conductive electrode material that are stable against mechanical deformation, a flexible and stretchable polymer semiconductor and conductor material may be used to minimize changes in electrical properties, including changes in resistance, current, or permittivity, under mechanical deformation including tension, contraction, twist, bending, flexing, and compression, and in addition, one or more semiconductor and conductor materials selected from the group consisting of an organic material, a polymer material, a metal oxide material, a phase change alloy material, a carbon material, a nitride material, a two-dimensional layered material, a material having a perovskite structure, a metallic material, an ionic dielectric material, and a mixture thereof may be formed in a shape selected from the group consisting of a thin film, microdots, microparticles, microflakes, microwires, microfibers, microfibrils, microwhiskers, microrods, microtubes, microbelts, nanodots, nanoparticles, nanoflakes, nanowires, nanofibers, nanofibrils, nanowhiskers, nanorods, nanotubes, and nanobelts.

At least one artificial synaptic device employed in the neuromorphic nerve device in accordance with the present disclosure may be attached to the skin of the body or inserted into the body. To this end, the thickness of the entire device including the substrate is 2000 μm or less, preferably 200 μm or less, and more preferably 100 μm or less. For special purposes, it is desirable to be 50 μm or less. The weight of the entire device including the substrate may be 500 g or less, preferably 200 g or less, more preferably 100 g or less, and for special purposes, 10 g or less.

The artificial synapse having the three or more terminal electrodes includes a semiconducting structure forming a channel region and an ion gel dielectric layer forming a dielectric layer between the channel region and a gate electrode.

The semiconducting structure may be an organic semiconducting structure based on an organic material and include an organic small molecule semiconductor, an organic polymer semiconductor, a conductive polymer, an insulating polymer, or a mixture thereof, and the organic small molecule semiconductor may be a small molecule material having a conjugated structure and having a band gap of usually 1.0 eV or more and 3.5 eV or less, or more broadly, 0.1 eV or more and less than 6.0 eV and be at least one selected from the group consisting of pentacene, TIPS-Pentacene (6,13-bis(triisopropylsilylethynyl) pentacene), rubrene, tetracene, anthracene, TES ADT (triethylsilylethynyl anthradithiophene), and PCBM ([6,6]-phenyl C61 butyric acid methyl ester), and the organic polymer semiconductor may be a polymer material having a conjugated structure and having a normal band gap of 1.0 eV or more and 3.5 eV, or more broadly, 0.1 eV or more and less than 6.0 eV, and be at least one selected from the group consisting of polythiophene, poly(3-hexylthiophene) (P3HT), poly 3-octlythiophene (P3OT), poly butylthiopehene (PBT), poly (3,4-ethylenedioxythiophene) (PEDOT), poly(9-vinylcarbazole) (PVK), poly(p-phenylene vinylene), poly(thienylene vinylene) (PTV), polyacetylene, polyfluorene, polyaniline, polypyrrole, a diketopyrrolopyrrole-based copolymer, an isoindigo-based copolymer, and a derivative thereof, and the insulating polymer may a polymer material having a band gap of 6.0 eV or more or insulating properties, and be one or more selected from the group consisting of polyethylene oxide (PEO), polystyrene (PS), polycaprolactone (PCL), polyacrylonitrile (PAN), poly(methyl methacrylate) (PMMA), polyimide, poly(vinylidene fluoride) (PVDF), polyvinylchloride (PVC), styrene-based copolymers, and a mixture thereof.

The organic semiconducting structure may be formed in a shape selected from the group consisting of a thin film, nanoparticles, nanowires, nanofibers, nanofibrils, nanowhiskers, nanorods, nanotubes, and nanobelts.

In accordance with the present disclosure, instead of the organic semiconducting structure, as an active material, the semiconducting structure may use one or more selected from the group consisting of a metal oxide material, a phase change alloy material, a carbon nanomaterial, a nitride material, a two-dimensional layered material, a material having a perovskite structure, a metal nanomaterial, nanoparticles, quantum dots, plate-like particles, nanowires, an ionic dielectric material, and a mixture thereof.

The ion gel dielectric layer includes an ionic dopant, and the ionic dopant is characterized in that polarization of positive and negative ions is formed or separated according to an applied electrical signal, and includes materials such as metals, ceramics, polymers, semiconductors, and dielectrics containing ions, but is not limited thereto. For example, the ion gel dielectric layer may include an ionic dopant selected from the group containing cations of 1-ethyl-3-methylimidazolium, 1-butyl-3-methylimidazolium, methyl-tributylammonium, 1,2,3-trimethylimidazolium, methylimidazolium, 1-ethyl-2,3-dimethylimidazolium, 1-butyl-2,3-dimethylimidazolium, 1-dodecyl-3-methylimidazolium, 1-butyl-1-methylpyrrolidinium, N-methyl-ntrioctylammonium, N-butyl-N-methylpyrrolidinium, triethylsulphonium, tetraethylammonium, tetrabutylphosphonium, methyltrioctylammonium, 3-methyl-1-propylpyridinium, 1,2-dimethyl-3-propylimidazolium, 1-hexyl-3-methylimidazolium, 1-methyl-3-octylimidazolium, 1-butyl-4-methylpyridinium, 1,3-dimethylimidazolium, 4-(3-butyl-1-imidazolio)-1-butanesulfonic acid, 3-(triphenylphosphonio) propane-1-sulfonic acid, 1-allyl-3-methylimidazolium, 1-butyl-1-(3,3,4,4,5,5,6,6,7,7,8,8,8-tridecafluorooctyl)-imidazolium, or 1-methyl-3-(3,3,4,4,5,5,6,6,7,7,8,8,8-tridecafluoro-octyl)-imidazolium, and anions of chloride, methanesulfonate, methylsulfate, hydrogensulfate, tetrachloroaluminate, acetate, methyl sulfate, thiocyanate, ethyl sulfate, tetrafluoroborate, dicyanamide, hexafluoroantimonate, hexafluorophosphate, bis(trifluoromethyl sulfonyl)imide, trifluoromethane sulfonate, iodide, nitrate, bromide, bis(pentafluoroethylsulfonyl)-imide, tosylate, octyl sulfate, bis(2,4,4-trimethyl-pentyl)phosphinate, decanoate, thiosalicylate, triflate2-(2-methoxyethoxy)-ethyl sulfate, nonafluorobutanesulfonate, benzoate, or heptadecafluorooctanesulfonate, or include a blend thereof. The ion gel dielectric is not particularly limited to a specific ionic dielectric material because all ionic dielectric materials and a mixture thereof may be included in the present disclosure.

The conductive electrode material stable against mechanical deformation may include at least one selected from the group consisting of a carbon nanomaterial, a metal nanomaterial, and a liquid metal, and is not limited thereto.

The artificial synaptic device may require an encapsulation process using materials including a polymer thin film, glass, stainless steel, an inorganic material, graphene, and a multi-layered organic/inorganic structure for protection and stable operation of the device depending on body insertion and external environment.

A water-soluble polymeric adhesive may be used to attach the artificial synaptic device to a surface of body skin, an organ, or an object.

In the artificial synaptic device, the substrate itself may be used as an ionic dielectric or semiconductor. The low-power stretchable neuromorphic nerve device may include a hydrogel electrode that functions as a bio-interface connected to the artificial synapse to apply a post-synaptic current to a living organ.

The hydrogel may include fibrin gel, collagen, agarose gel, matrigel, puramatrix, poly vinyl alcohol (PVA), poly(ethylene glycol) methacrylate (PEGMA), poly(ethylene glycol) diacrylate (PEGDA), alginate, 2-hydroxyethyl methacrylate (HEMA), polyacrylic acid, polyacrylamide, and a mixture thereof.

The hydrogel may include polyaniline, polypyrrole, poly(3,4-ethylenedioxythiophene) (PEDOT), a carbon nanomaterial, a metal nanomaterial, an ionic dielectric material, and a mixture thereof as a conductive filler.

The low-power stretchable neuromorphic nerve device in accordance with the present disclosure may be connected to the artificial synapse, and may include a resistor and an amplifier, and the amplifier may be a current-to-voltage amplifier that amplifies a post-synaptic current.

Another aspect of the present disclosure relates to a low-power neuromorphic prosthetic device including the above-described low-power stretchable neuromorphic nerve device in accordance with the present disclosure and a remote controller for remotely controlling operation of the neuromorphic nerve device.

BRIEF DESCRIPTION OF THE DRAWINGS

Exemplary embodiments can be understood in more detail from the following description taken in conjunction with the accompanying drawings, in which.

Figure 5:
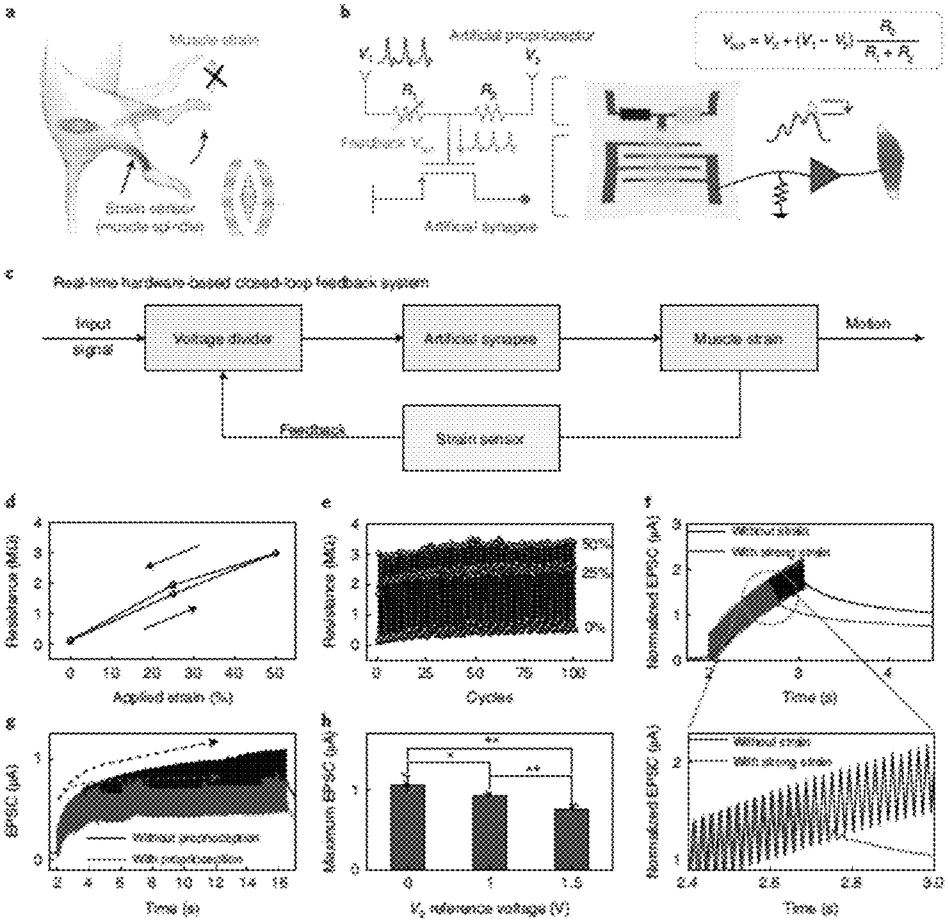
Figure 6:
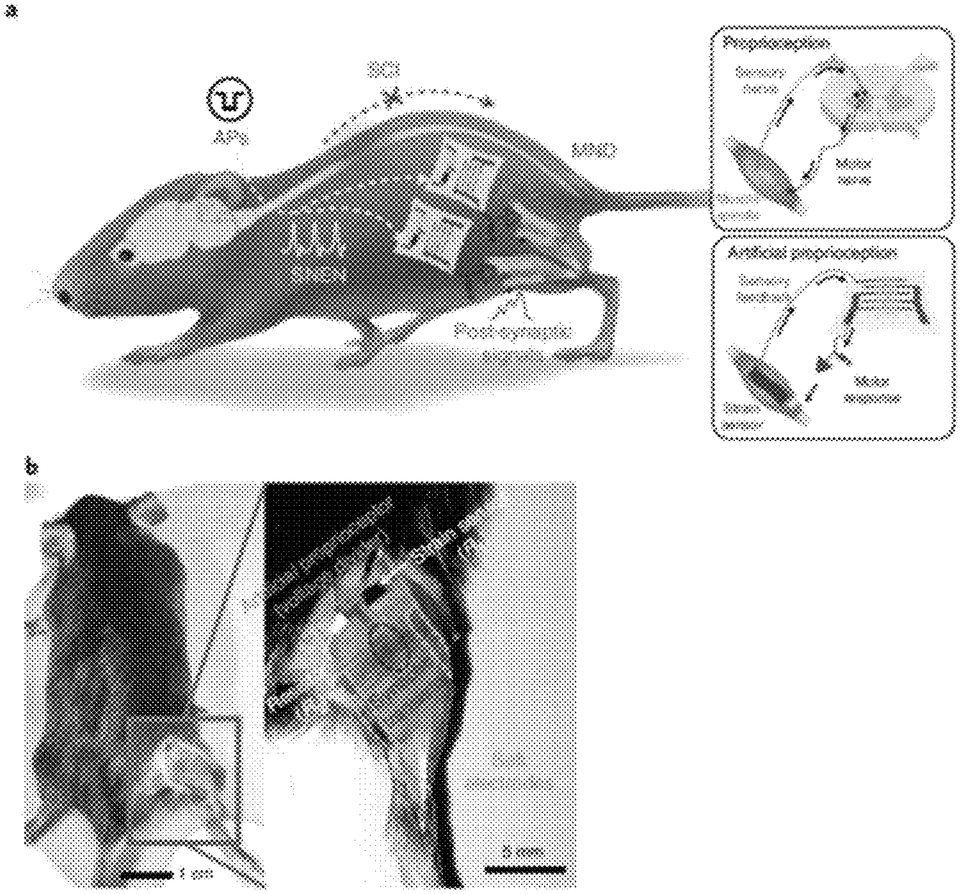
Figure 7:
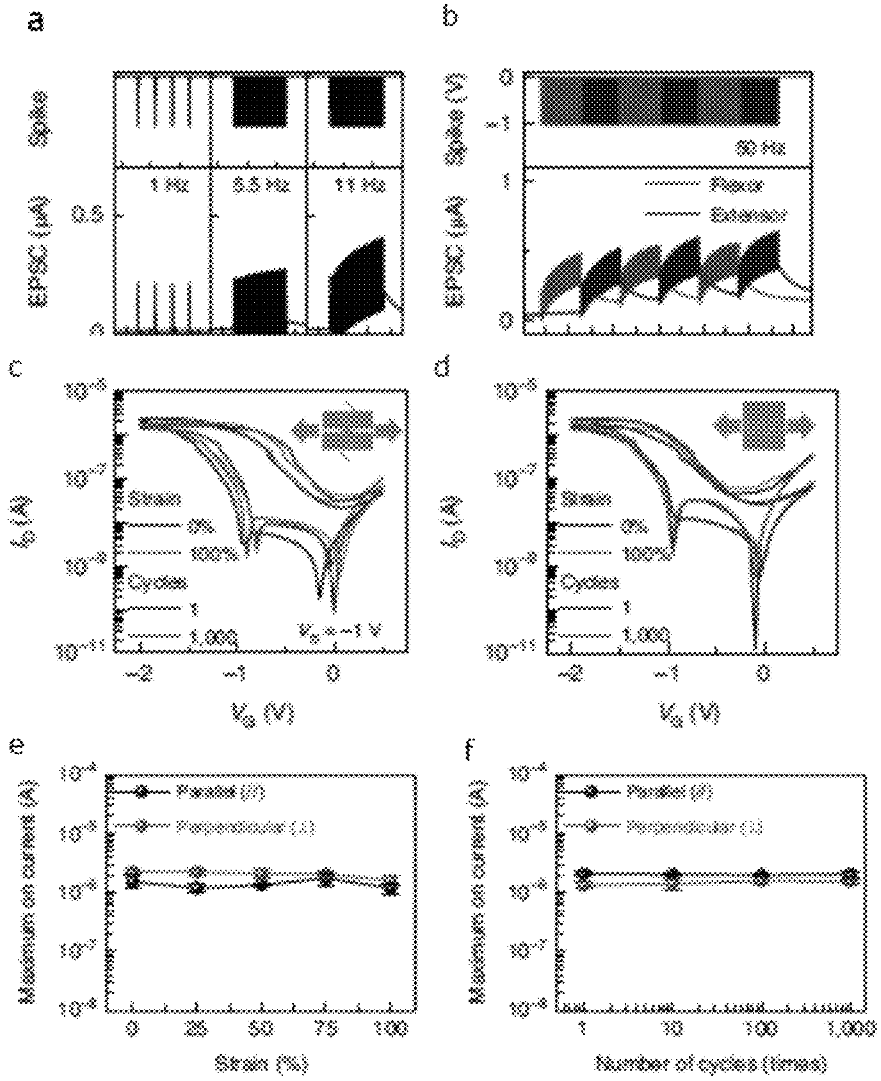
Figure 8:
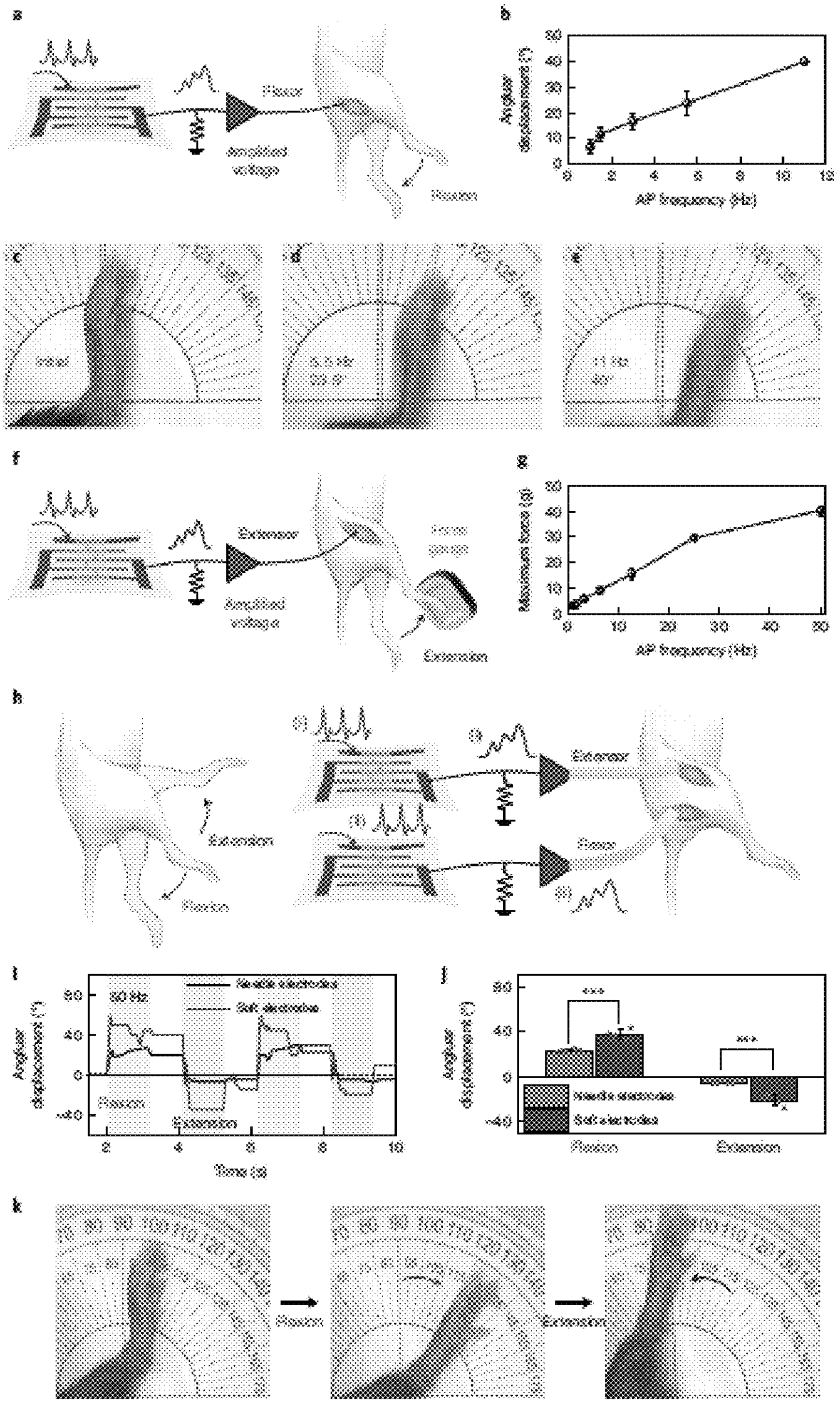
Figure 9:
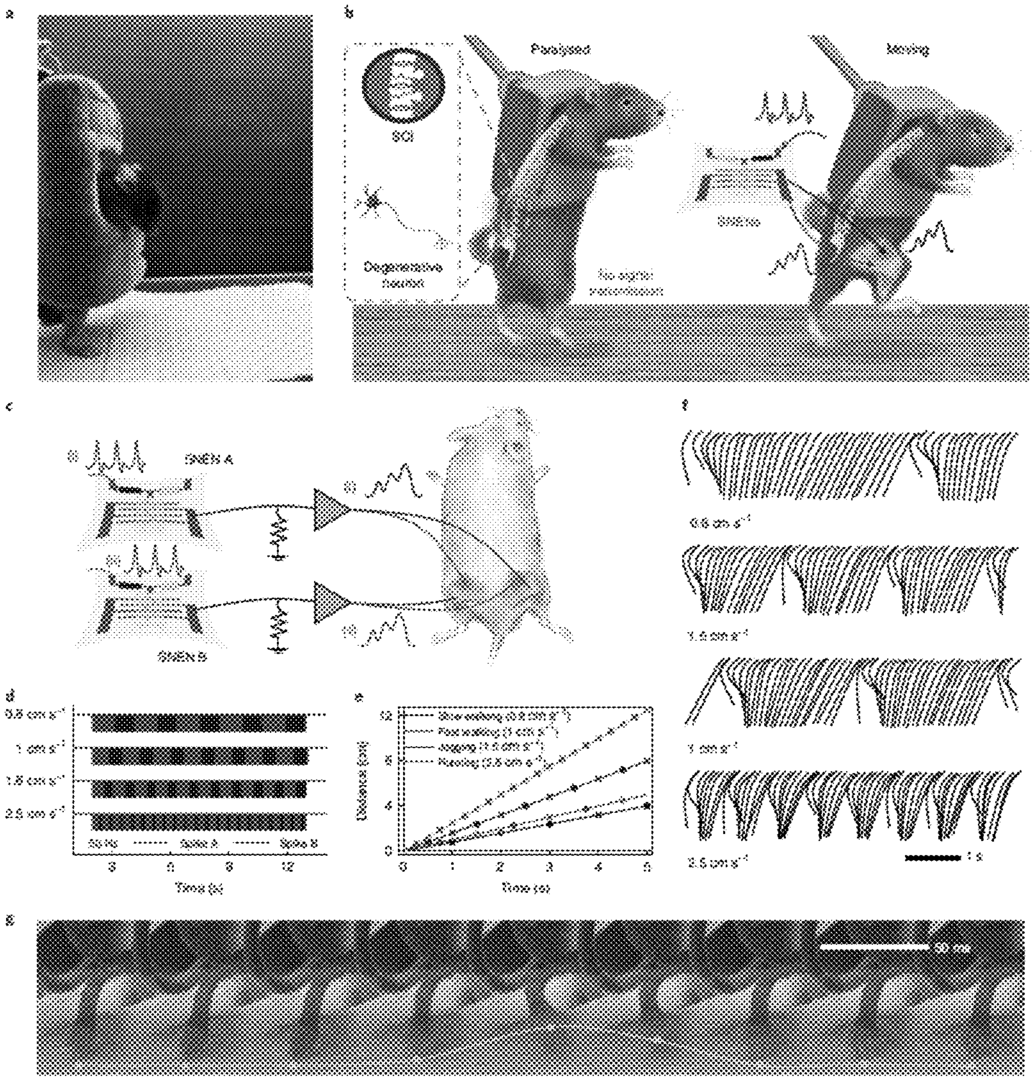
Figure 10:
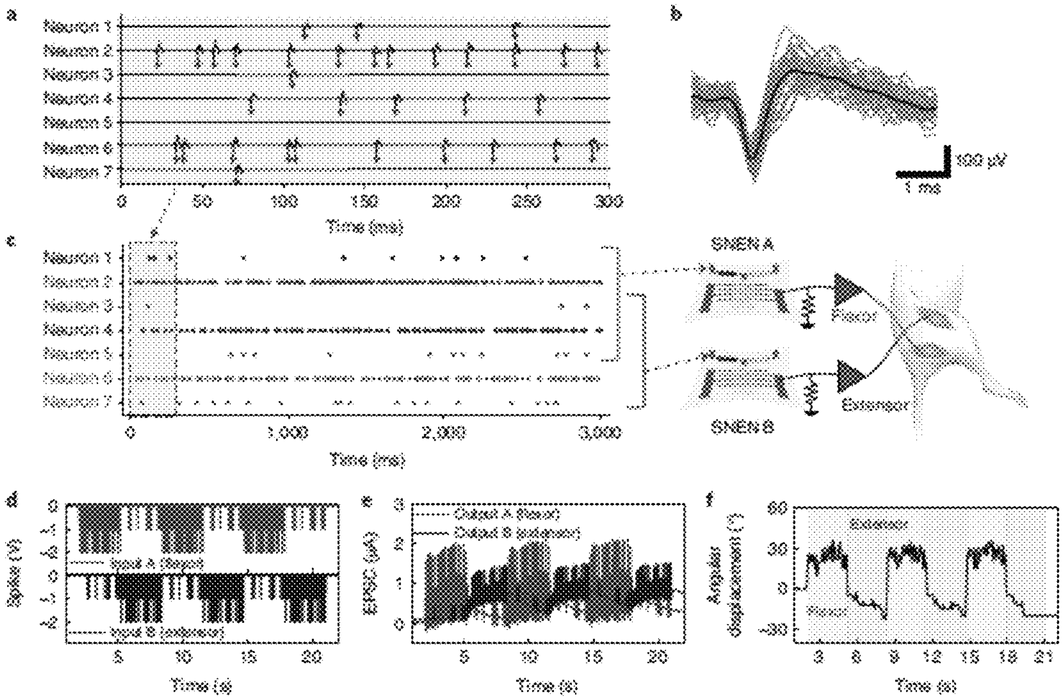
Figure 11:
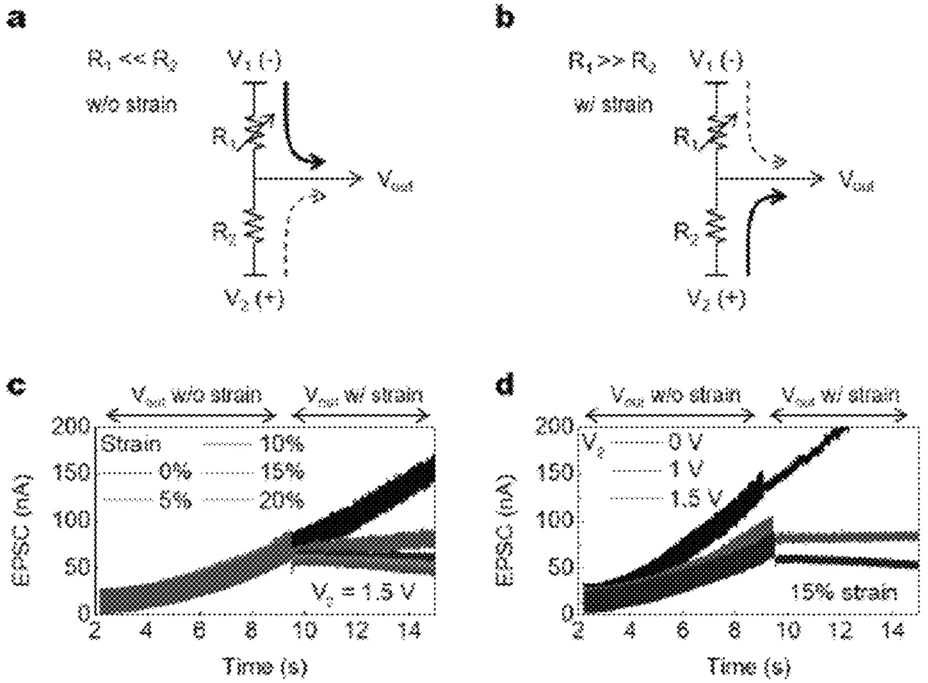
Figure 12:
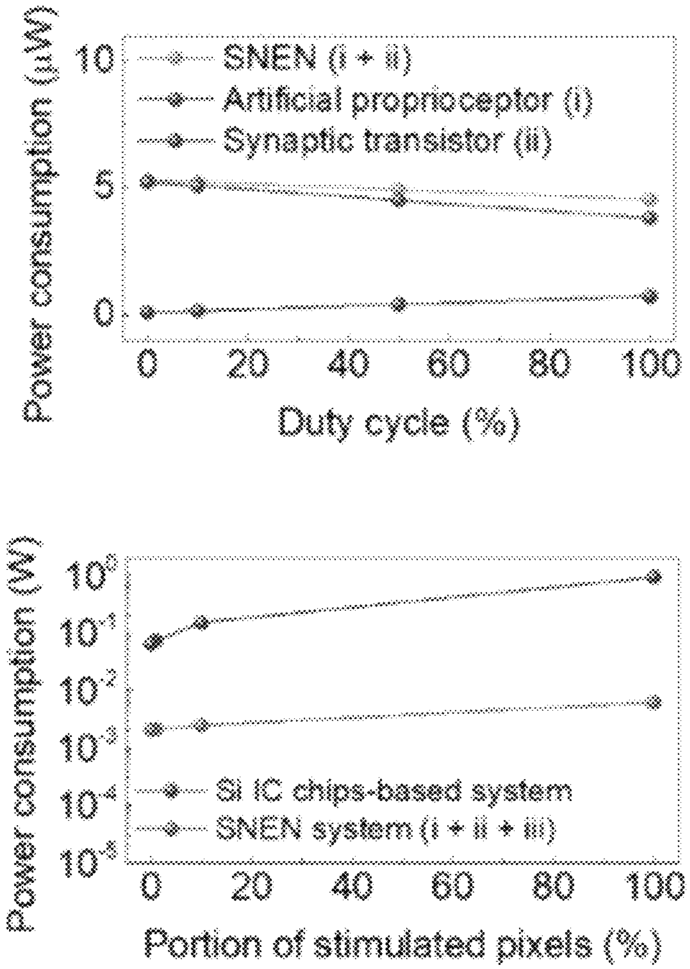
Figure 13:
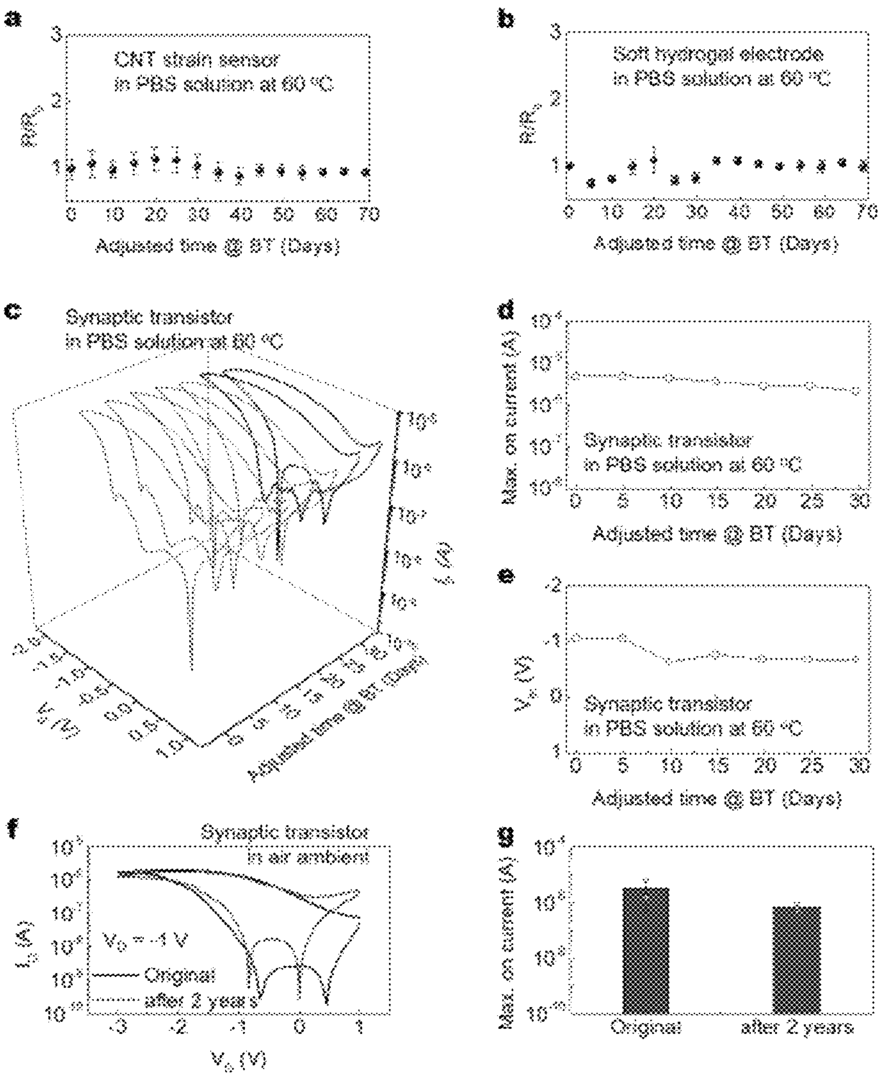

(a) and (b) of FIG. 5 are views for describing the concept of an artificial muscle spindle-based proprioceptive feedback loop that prevents muscle damage due to excessive tension, (c) of FIG. 5 is a block diagram of a real-time hardware closed-loop feedback system of an artificial proprioceptor device, (d) and (e) of FIG. 5 are graphs showing resistance change of a carbon nanotube (CNT) strain sensor, (f) of FIG. 5 is a graph showing a normalized excitatory post-synaptic current (EPSC) ($I-I_{Baseline}$) in the case of strong strain (red) and in the case of no strain (black), (g) of FIG. 5 illustrates EPSCs in the case of no proprioceptive feedback (black) and in the case of proprioceptive feedback (red), and (h) of FIG. 5 illustrates a maximum EPSC modulated by proprioceptive feedback by a reference voltage ($V_2$):

(a) of FIG. 6 is a schematic view of an artificial nerve device (herein referred to as a stretchable neuromorphic efferent nerve (SNEN)) in accordance with an exemplary embodiment of the present disclosure based on an artificial synapse that bypasses damaged nerves and transmits nerve signals to muscles and (b) of FIG. 6 is a photograph of an anesthetized mouse with the SNEN attached to its leg:

(a) of FIG. 7 is a graph illustrating pre-synaptic voltage spikes applied to a gate electrode and EPSCs read by a drain electrode, and (c) and (d) of FIG. 7 are graphs illustrating current-voltage characteristic curves shown when the artificial synapse is stretched in vertical and horizontal directions and changes in maximum current values:

(a) of FIG. 8 is a view illustrating that a hind limb flexor muscle is stimulated with an artificial efferent nerve, (b) of FIG. 8 illustrates an angular displacement of the hind limb stimulated with an action potential firing frequency ($f_{AP}$) from 1 Hz to 11 Hz, (c) to (e) of FIG. 8 are leg exercise photographs when $f_{AP}$ is 0 (c), 5.5 (d), and 11 Hz (e), (f) of FIG. 8 is a view illustrating stimulation of extensor muscles of a hind limb of a mouse with an artificial efferent nerve, (g) of FIG. 8 is a graph illustrating a maximum force of the hind limb according to $f_{AP}$ from 1 Hz to 50 Hz, (h) of FIG. 8 is a view illustrating stimulation of the extensor muscles and flexors of the hind limb with two artificial efferent nerves, one nerve connecting to the extensor muscles, the other nerve connecting to the flexors, (i) and (j) of FIG. 8 are graphs illustrating angular displacement (i) and uniformity (j) of the hind limb according to alternate stimulation of flexion and extension using a needle electrode (25G) and a flexible electrode, and (k) of FIG. 8 illustrates photographs of a leg exercise with flexion and extension:

(a) and (b) of FIG. 9 are photographs of a mouse paralyzed and a mouse capable of bipedal walking by attaching the neuromorphic nerve device in accordance with an exemplary embodiment of the present disclosure, (c) of FIG. 9 is a configuration diagram of a mouse for bipedal walking locomotion, (d) of FIG. 9 is pre-synaptic input spike patterns according to different movement speeds, (e) of FIG. 9 illustrates movement distances, (f) of FIG. 9 illustrates kinematic trajectories of the mouse hind limb according to different movement speeds, and (g) of FIG. 9 is a photochronography of the hind limb during bipedal walking:

(a) to (c) of FIG. 10 illustrate electrophysiological data sampled from seven single-unit recorded neurons in a primary motor cortex of a moving animal, (d) and (e) of FIG. 10 illustrate pre-synaptic voltage spikes and EPSCs of the artificial synapse, and (f) of FIG. 10 is a graph illustrating angular displacement of the hind limb according to alternate stimulation of the flexors (flexion) and extensor muscles (extension);

FIG. 11 illustrates graphs of preliminary evaluation results of a negative feedback loop, where (a) is a circuit diagram of a strain-free voltage divider ($R_1 \ll R_2$) and (b) of FIG. 11 is a circuit diagram of the voltage divider ($R_1 \gg R_2$) in a preliminary test state for an EPSC response with strain, and (c) and (d) of FIG. 11 are graphs illustrating results of a preliminary test on the EPSC response of the artificial synapse:

FIG. 12 illustrates graphs of comparisons between power consumption of the neuromorphic nerve device (SNEN) of the present disclosure and power consumption of a system composed of a silicon integrated circuit chip; and FIG. 13 illustrates graphs of long-term stability test results of a CNT strain sensor and a soft hydrogel electrode of the neuromorphic nerve device of the present disclosure.

DETAILED DESCRIPTION OF EMBODIMENTS

Hereinafter, exemplary embodiments will be described in more detail with reference to the accompanying drawings.

In the present specification, expressions of singular form are intended to include meanings of plural forms as well, unless the context clearly indicates otherwise. In the present specification, the terms "includes" and/or "have" are intended to designate the presence of specific features, numbers, steps, operations, elements, components, and/or combinations thereof, but do not intend to preclude the presence or addition of one or more other features, numbers, steps, operations, elements, components, and/or combinations thereof.

It will be understood that when an element is referred to as being "coupled" or "connected" to another element, the element may be directly coupled or connected to the other element, or intervening elements may also be present.

A low-power stretchable neuromorphic nerve device in accordance with the present disclosure may be referred to as a stretchable neuromorphic efferent nerve (SNEN) device using a stretchable artificial synapse. In the present specification, the term "low-power stretchable neuromorphic nerve device" and the term "stretchable neuromorphic efferent nerve" are used interchangeably and may be abbreviated as "SNEN." The neuromorphic nerve device in accordance with the present disclosure may be implanted or connected to a living organ to deliver stimulation to a biological motor organ or restore or control movement of the biological motor organ. The word "stretchable" is used when a flexible material has an elongation property, and usually exhibits a property of stretching from 3% to 1,000%, or more broadly from 1% to 10,000%. In order to apply the word to the human body, at least a range of 5% to 50%, preferably a range of 10% to 100%, and more preferably a range of 20% to 500% should be satisfied.

Figure 1:
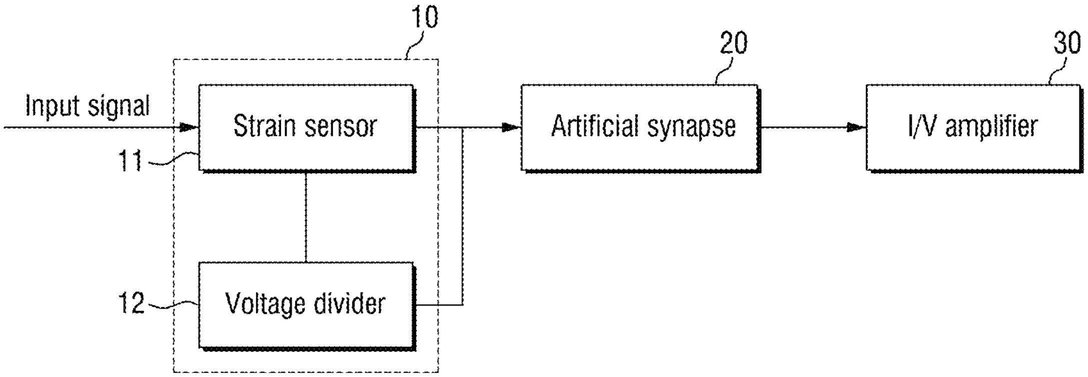
FIG. 1 is a block diagram schematically illustrating a low-power stretchable neuromorphic nerve device in accordance with an exemplary embodiment of the present disclosure.
Figure 2:
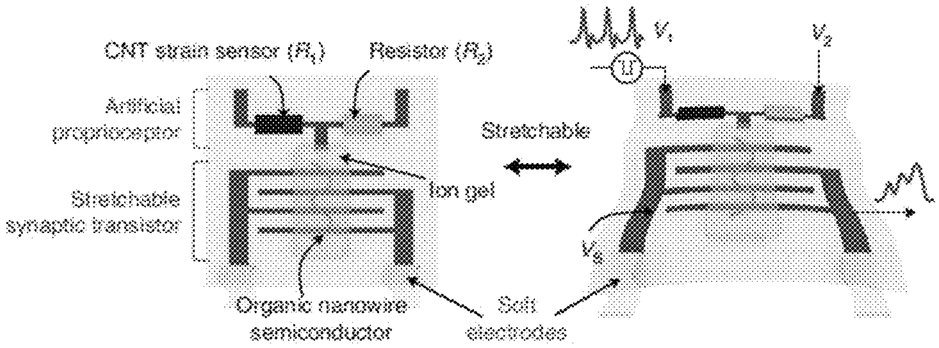
FIG. 2 is a schematic diagram of the low-power stretchable neuromorphic nerve device in accordance with an exemplary embodiment of the present disclosure.
Figure 3:
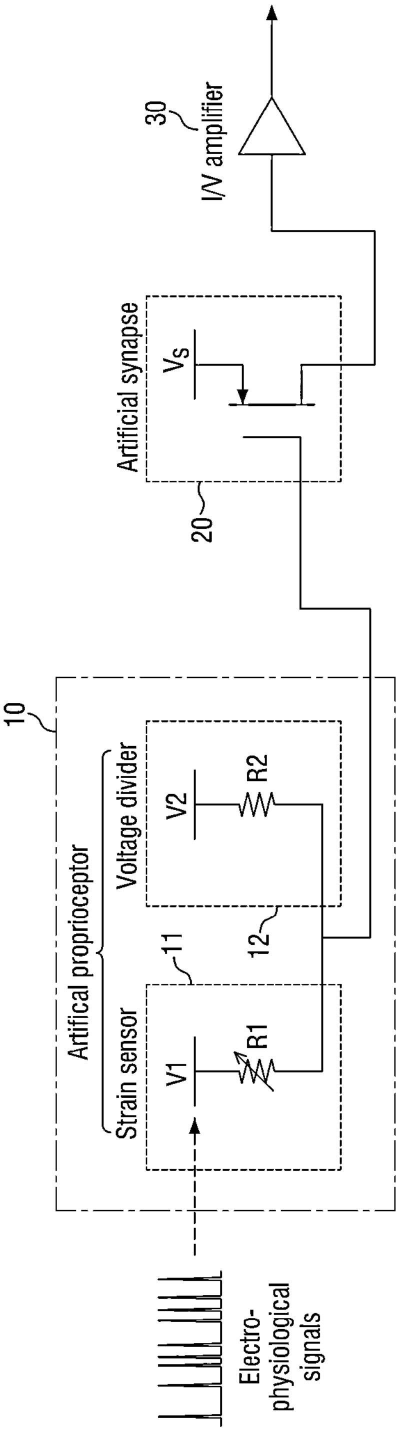
FIG. 3 is a circuit diagram of the low-power stretchable neuromorphic nerve device in accordance with an exemplary embodiment of the present disclosure.

FIG. 1 is a schematic block diagram of a low-power stretchable neuromorphic nerve device in accordance with an exemplary embodiment of the present disclosure, FIG. 2 is a schematic diagram of the low-power stretchable neuromorphic nerve device in accordance with an exemplary embodiment of the present disclosure, and FIG. 3 is a circuit diagram of the low-power stretchable neuromorphic nerve device according to an exemplary embodiment of the present disclosure.

Referring to FIG. 1, the low-power stretchable neuromorphic nerve device for transmitting electrophysiological signals to biological motor organs or restoring or controlling motion of biological motor organs in accordance with an exemplary embodiment of the present disclosure is a low-power stretchable neuromorphic nerve device for transmitting stimuli to biological motor organs or restoring or controlling motion of biological motor organs and includes an artificial proprioceptor device 10 that emulates an animal's proprioceptor and provides proprioceptive feedback for nerve stimulation and an artificial synapse 20 that receives a signal from the artificial proprioceptor device 10 and outputs, to a living organ, a post-synaptic signal capable of controlling the living organ, and the artificial proprioceptor device 10 forms a closed feedback loop together with the artificial synapse 20. The closed feedback loop may be a closed negative feedback loop or a closed positive feedback loop. The animal's proprioceptor may be a muscle spindle or a golgi tendon organ.

A strain sensor 11 of the artificial proprioceptor device 10 emulates the animal's proprioceptor, for example, a biological muscle spindle, detects a change in leg (muscle) length, and activates the negative feedback loop. The artificial synapse 20 serves to control and stimulate motor organs (living organs) such as limbs by processing input signals received from muscle strains.

The low-power stretchable neuromorphic nerve device in accordance with the present disclosure uses the principle of neuroplasticity. The artificial synapse 20 in accordance with the present disclosure emulates short-term plasticity of a biological synapse and exhibits a reaction in which the output signal gradually increases as connection is strengthened in the short term by repeated application of spikes. In the electrochemical artificial synapse using the semiconducting structure in accordance with an exemplary embodiment of the present disclosure and an ion gel dielectric layer, electric charges are induced inside the semiconducting structure by a gate voltage that simulates a pre-synaptic action potential, and thus the electrochemical artificial synapse exhibits a drain current response that emulates a post-synaptic action potential. As a short-time gate voltage is repeatedly applied, the amount of ions accumulated on a surface of or inside of the semiconducting structure gradually increases, and as a result, a synaptic potentiation response appears in which the magnitude of a drain current also increases.

The artificial proprioceptor device 10 in accordance with the present disclosure includes one or more sensors 11 selected from the group consisting of a strain sensor for detecting muscle length and force, a pressure sensor, an optical sensor, an image sensor for detecting visual information, an acceleration sensor for detecting balance, and a gyroscope sensor, and a voltage divider 12 for adjusting an output voltage of the artificial proprioceptor device 10. The artificial proprioceptor device 10 detects movement and prevents excessive stretching of the muscles. The voltage divider includes one or more resistors and one or more voltage sources, and the one or more resistors may include a variable resistor ($R_1$) and a fixed resistor ($R_2$).

In the neuromorphic nerve device in accordance with the present disclosure, the artificial proprioceptor device 10 forms a closed feedback loop system together with the artificial synapse 20. The closed feedback loop system may be formed so that the strain sensor 11 of the artificial proprioceptor device 10 is able to receive an input on muscle deformation when the muscle is deformed. Such an input may be related to physiological signals, such as physiological electrical signals from a patient. Stimulation may be better adapted to the needs of the patient using physiological feedback provided by the patient that is stimulated by the neuromorphic nerve device in accordance with the present disclosure.

The strain sensor 11 may be a carbon nanotube strain sensor, and in addition to the carbon nanotubes, may include one or more conductive or semiconducting materials selected from the group consisting of carbon nanofibers, carbon black, graphene, two-dimensional (2D) materials (graphene, transition metal dichalcogenide (e.g., $MoS_2$), MXene, graphene oxide, inorganic semiconductor membrane (e.g., Si membrane), or the like), a metal film crack sensor, metal nanowires, metal nanoparticles, conjugated polymers, metal oxide nanoparticles, metal oxide thin films, metal oxide nanowires, and semiconducting nanowires.

The strain sensor 11 may be one or more selected from the group consisting of a piezoresistive strain sensor, a piezoelectric strain sensor, a triboelectric strain sensor, and a capacitive strain sensor that change electrical signals by changing resistance, current, voltage, and permittivity according to strain stimulation or change optical characteristics by changing light transmittance and light absorption, but is not necessarily limited thereto.

The pressure sensor may include a sensor that detects external light, pressure, touch, friction, sound, vibration, or heat and converts it into an electrical signal. The pressure sensor may be a sensor that changes an electrical signal by changing resistance, current, voltage, or permittivity according to an intensity of applied pressure or changes optical characteristics by changing light transmittance or light absorption.

A substrate of the pressure sensor may include at least one selected from the group consisting of silicon, glass, sapphire, polyimide, polyethylene terephthalate, polyethylene naphthalate, polycarbonate, polyacrylate, polyethersulfone, polypropylene, polydimethylsiloxane, polymethylphenylsiloxane, polydiphenylsiloxane, polysiloxane, polyurethane, polystyrene, a styrene butadiene copolymer, a polystyrene copolymer, and ecoflex, and is not limited thereto.

The artificial synapse 20 in accordance with the present disclosure may include the semiconducting structure forming a channel region, the ion gel dielectric layer forming a dielectric layer between the channel region and a gate electrode, and source and drain electrodes connected to the channel region.

The artificial synapse 20 may include a gate electrode formed on a substrate, an ion gel dielectric layer that insulating the gate electrode, a source electrode formed on the ion gel dielectric layer, a drain electrode, and semiconducting structure that connects the source electrode and the drain electrode, and the semiconducting structure may include an organic semiconductor.

The source electrode and the drain electrode may include one or more types of carbon nanotubes selected from the group consisting of single-walled carbon nanotubes, double-walled carbon nanotubes, multi-walled carbon nanotubes, and bundled carbon nanotubes.

The semiconducting structure may be an organic semiconducting structure based on an organic material and include an organic small molecule semiconductor, an organic polymer semiconductor, a conductive polymer, an insulating polymer, or a mixture thereof, and the organic small molecule semiconductor may be a small molecule material having a conjugated structure and having a band gap of 1.0 eV or more and 3.5 eV or less, or more broadly, 0.1 eV or more and 6.0 eV or less and be at least one selected from the group consisting of pentacene, TIPS-Pentacene (6,13-bis(triisopropylsilylethynyl) pentacene), rubrene, tetracene, anthracene, TES ADT (triethylsilylethynyl anthradithiophene), and PCBM ([6,6]-phenyl C61 butyric acid methyl ester), and the organic polymer semiconductor may be a polymer material having a conjugated structure and having a band gap of 1.0 eV or more and 3.5 eV or less, or more broadly, 0.1 eV or more and 6.0 eV or less, and be at least one selected from the group consisting of polythiophene, P3HT (poly(3-hexylthiophene)), P3OT (poly 3-octlythiophene), PBT (poly butylthiopehene), PEDOT (poly(3,4-ethylenedioxythiophene)), PVK (poly(9-vinylcarbazole)), poly(p-phenylene vinylene), PTV (poly(thienylene vinylene)), polyacetylene, polyfluorene, polyaniline, polypyrrole, diketopyrrolopyrrole-based copolymers, isoindigo-based copolymers, and derivatives thereof, and the insulating polymer may a polymer material having a band gap of 6.0 eV or more or insulating properties, and be one or more selected from the group consisting of polyethylene oxide (PEO), polystyrene (PS), polycaprolactone (PCL), polyacrylonitrile (PAN), poly(methyl methacrylate) (PMMA), polyimide, poly(vinylidene fluoride) (PVDF), polyvinylchloride (PVC), styrene-based copolymers, and a mixture thereof; however, they are not necessarily limited thereto.

The organic semiconducting structure may be formed in one or more shapes selected from the group consisting of a thin film, nanoparticles, nanowires, nanofibers, nanofibrils, nanowhiskers, nanorods, nanotubes, and nanobelts, but is not necessarily limited to the shapes.

In accordance with the present disclosure, instead of the organic semiconducting structure, as an active material, the semiconducting structure may use one or more selected from the group consisting of a metal oxide material, a phase change alloy material, a carbon nanomaterial, a nitride material, a two-dimensional layered material, a material having a perovskite structure, a metal nanomaterial, nanoparticles, quantum dots, plate-like particles, nanowires, an ionic dielectric material, and a mixture thereof.

The metal oxide material may be selected from the group consisting of zinc oxide, indium oxide, tin oxide, gallium oxide, tungsten oxide, aluminum oxide, titanium oxide, vanadium oxide, molybdenum oxide, and combinations thereof, and is not particularly limited to a specific metal oxide because all inorganic semiconductor materials and a mixture thereof may be included in the present disclosure.

The phase change alloy material may be selected from the group consisting of group 16 chalcogen elements including selenium (Se) and tellurium (Te) and a mixture thereof, and is not particularly limited to a specific phase change alloy material because all phase change alloy materials and a mixture thereof may be included in the present disclosure.

The carbon nanomaterial may be selected from the group consisting of carbon nanotubes, graphene, reduced graphene oxide, graphene quantum dots, graphene nanoribbons, carbon nitride ($C_3N_4$), amorphous carbon graphite, and a mixture thereof, and is not particularly limited to a specific carbon nanomaterial because all carbon nanomaterials and mixtures thereof may be included in the present disclosure.

The two-dimensional layered material may be selected from the group consisting of boron, carbon, nitrogen, hexagonal boron nitride, germanium, sulfur, phosphorus, molybdenum, tin, and a mixture thereof (e.g., transition metal dichalcogenide (TMDC)), and is not particularly limited to a specific two-dimensional layered material because all two-dimensional layered materials and a mixture thereof may be included in the present disclosure.

The nitride material included in at least one artificial synapse may be selected from the group consisting of carbon nitride ($C_3N_4$), aluminum nitride (AlN), gallium nitride (GaN), indium nitride (InN), titanium nitride (TiN), chromium nitride ($Cr_2N$), and a mixture thereof, and is not particularly limited to a specific nitride material because all nitride materials and a mixture thereof may be included in the present disclosure.

The material having the perovskite structure ($ABX_3$, a structure in which face-centered cubic and body-centered cubic crystal structures are mixed) includes inorganic metal oxides, inorganic metal halides, and organic-inorganic metal halides. These inorganic metal oxides are generally oxides, and materials in which metal cations such as Ti, Sr, Ca, Cs, Ba, Y, Gd, La, Fe, and Mn (alkali metals, alkaline earth metals, transition metals, lanthanum groups, or the like) having different sizes are located at A and B sites and oxygen anions are located at an X site, and the metal cations of the B site are combined with oxygen anions of the X site in the form of a corner-sharing octahedron of 6-fold coordination. Examples thereof include $SrFeO_3$, $LaMnO_3$, and $CaFeO_3$.

The ion gel dielectric includes an ionic dopant, and the ionic dopant is characterized in that polarization of positive and negative ions is formed or separated according to an applied electrical signal, and includes materials such as metals, ceramics, polymers, semiconductors, and dielectrics containing ions, but is not limited thereto. For example, the ion gel dielectric may include an ionic dopant selected from the group containing cations of 1-ethyl-3-methylimidazolium, 1-butyl-3-methylimidazolium, methyl-tributylammonium, 1,2,3-trimethylimidazolium, methylimidazolium, 1-ethyl-2,3-dimethylimidazolium, 1-butyl-2,3-dimethylimidazolium, 1-dodecyl-3-methylimidazolium, 1-butyl-1-methylpyrrolidinium, N-methyl-ntrioctylammonium, N-butyl-N-methylpyrrolidinium, triethylsulphonium, tetraethylammonium, tetrabutylphosphonium, methyltrioctylammonium, 3-methyl-1-propylpyridinium, 1,2-dimethyl-3-propylimidazolium, 1-hexyl-3-methylimidazolium, 1-methyl-3-octylimidazolium, 1-butyl-4-methylpyridinium, 1,3-dimethylimidazolium, 4-(3-butyl-1-imidazolio)-1-butanesulfonic acid, 3-(triphenylphosphonio) propane-1-sulfonic acid, 1-allyl-3-methylimidazolium, 1-butyl-1-(3,3,4,4,5,5,6,6,7,7,8,8,8-tridecafluorooctyl)-imidazolium, or 1-methyl-3-(3,3,4,4,5,5,6,6,7,7,8,8,8-tridecafluoro-octyl)-imidazolium, and anions of chloride, methanesulfonate, methylsulfate, hydrogensulfate, tetrachloroaluminate, acetate, methyl sulfate, thiocyanate, ethyl sulfate, tetrafluoroborate, dicyanamide, hexafluoroantimonate, hexafluorophosphate, bis(trifluoromethyl sulfonyl)imide, trifluoromethane sulfonate, iodide, nitrate, bromide, bis (pentafluoroethylsulfonyl)-imide, tosylate, octyl sulfate, bis (2,4,4-trimethyl-pentyl)phosphinate, decanoate, thiosalicylate, triflate2-(2-methoxyethoxy)-ethyl sulfate, nonafluorobutanesulfonate, benzoate, or heptadecafluorooctanesulfonate, or include a blend thereof. The ion gel dielectric is not particularly limited to a specific ionic dielectric material because all ionic dielectric materials and a mixture thereof may be included in the present disclosure.

The ion gel dielectric layer may include a polymer having a property of being gelled by being cured by an ionic liquid, heat, and ultraviolet rays.

At least one artificial synapse employed in the neuromorphic nerve device in accordance with the present disclosure may be attached to the skin of the body or inserted into the body. To this end, the thickness of the entire device including the substrate may be 2000 μm or less, preferably 200 μm or less, and more preferably 100 μm or less. In addition, the weight of the entire device including the substrate may be 500 g or less, preferably 200 g or less, and more preferably 100 g or less.

The low-power stretchable neuromorphic nerve device in accordance with the present disclosure may include a hydrogel electrode that functions as a bio-interface connected to the artificial synapse to apply a post-synaptic current to a living organ.

The hydrogel may include one or more selected from the group consisting of fibrin gel, collagen, agarose gel, matrigel, puramatrix, poly vinyl alcohol (PVA), poly(ethylene glycol) methacrylate (PEGMA), poly(ethylene glycol) diacrylate (PEGDA), alginate, 2-hydroxyethyl methacrylate (HEMA), polyacrylic acid, polyacrylamide gel, and a mixture thereof.

The low-power stretchable neuromorphic nerve device in accordance with the present disclosure may include a resistor and an amplifier, and the amplifier may be a current-to-voltage amplifier 30 that amplifies a post-synaptic current. An electrical signal amplified by the current-voltage amplifier 30 is applied to one or more hydrogel electrodes connected to a living organ.

The neuromorphic nerve device in accordance with the present disclosure may be connected to, for example, the sensory or motor nervous system and used to preserve or study functions of the damaged sensory or motor nervous system or treat the damaged sensory or motor nervous system. Furthermore, for example, the bio-linked neuromorphic nerve device may be connected to the sensory or motor nervous system to control the secretion of non-ideal neurotransmitters in the sensory or motor nervous system, or may be used to study or treat spinal cord injury, Parkinson's disease, Lou Gehrig's disease, myasthenia gravis, Hansen's disease, or other neurodegenerative diseases by being substituted for a degenerated sensory or motor neuron or nerve, and synapse.

In addition, the neuromorphic nerve device in accordance with the present disclosure may be applied to robot development and prosthetic devices when an artificial sensory or motor nervous system device is created, through which an intelligent soft robot or wearable electronic device may be fabricated.

Another aspect of the present disclosure relates to a low-power neuromorphic prosthetic device including the low-power stretchable neuromorphic nerve device in accordance with the present disclosure and a controller for remotely controlling operation of the neuromorphic nerve device. The stretchable neuromorphic prosthetic device in accordance with the present disclosure may be used to improve or restore movement or movement ability of a patient to whom the device is mounted. For example, the mounting place of the device includes toes, fingers, arms, feet, legs or limbs of a patient, but is not necessarily limited to these living organs.

Operations of the low-power stretchable neuromorphic nerve device in accordance with the present disclosure will be described.

The low-power stretchable neuromorphic nerve device in accordance with the present disclosure may be connected to biological motor organs such as biological muscular fibers, biological motor units (motor neurons and muscle fibers connected thereto), biological motor neurons, and biological neuromuscular junctions. The low-power stretchable neuromorphic nerve device in accordance with the present disclosure may be desirably implanted or connected to living organs to control the biological motor organs in response to external pressure stimuli.

A basic function of the neuron is to transmit information to other cells through the synapse by generating electrical spikes when stimulated above a threshold. An electrical signal generated in this way is called an action potential (AP). The synapse not only transmits excitation, but also causes summation or inhibition according to the temporal/spatial changes of the excitation that arrive at the synapse, enabling higher-order integration of the nervous system.

In the low-power stretchable neuromorphic nerve device in accordance with the present disclosure, an action potential (AP) signal is applied to the artificial proprioceptor device 10 and then transmitted to the artificial synapse 20. The strain sensor 11 generates an electrical signal simulating the action potential and applies the generated signal to the gate electrode as a pre-synaptic action potential of the artificial synapse 20. In addition, the strain sensor 11 detects muscle strain and adjusts the output voltage of the voltage divider 12 of the artificial proprioceptor device 10. As the pre-synaptic gate voltage spike AP increases at the artificial synapse 20, an excitatory post-synaptic current (EPSC) at the drain electrode increases. This response emulates synaptic potentiation of the biological synapse.

Figure 4:
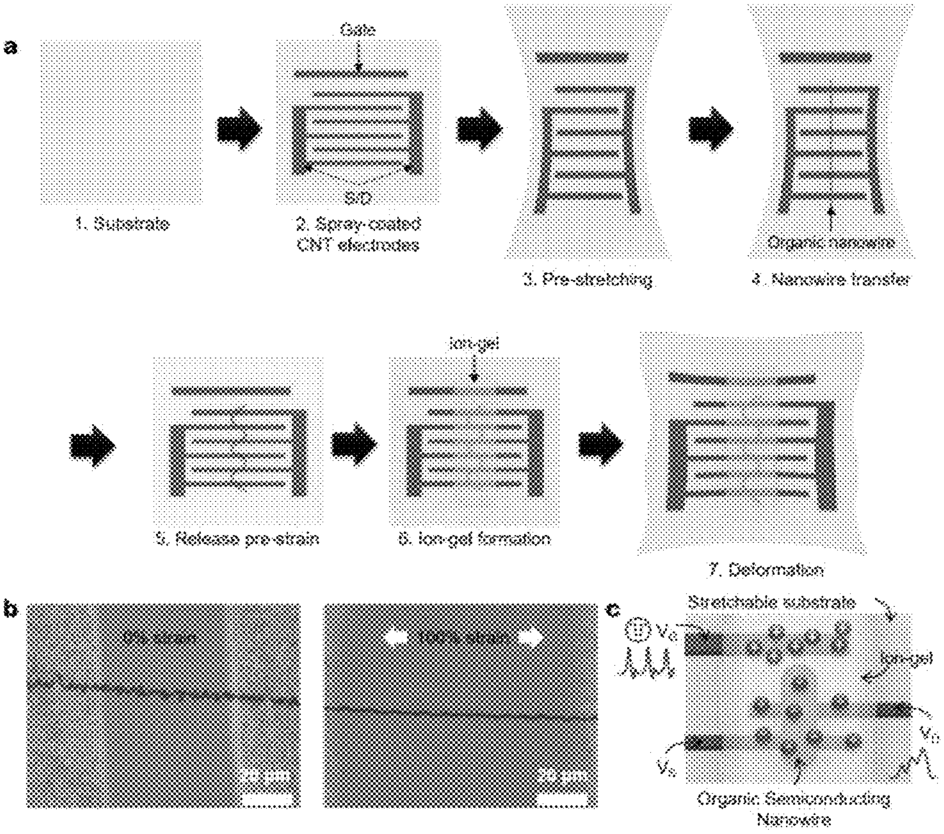
FIG. 4 illustrates views for describing a fabricating process of an artificial synapse of the low-power stretchable neuromorphic nerve device in accordance with an exemplary embodiment of the present disclosure.

When a pre-synaptic gate voltage ($V_G$) pulse is applied to the gate electrode of the artificial synapse 20, negative ions of the ion gel dielectric layer move and accumulate near the semiconducting structure (see (c) of FIG. 4). Holes are temporarily induced from the source electrode to the semiconducting structure to generate the excitatory post-synaptic current (EPSC), and such a post-synaptic signal is amplified and then applied to the muscles.

(c) of FIG. 5 is a diagram illustrating a real-time hardware-based closed-loop feedback system. Referring to (c) of FIG. 5, the low-power stretchable neuromorphic nerve device in accordance with the present disclosure employs a closed negative feedback mechanism by simulating a muscle spindle. The excitatory post-synaptic current (EPSC) may be adjusted at a lower level by leg extension and an increase in a resistor ($R_1$) of the strain sensor. With a large variation, a voltage divider circuit increases $R_1$ ($V_2$=0 V), lowering an effective gating voltage for the artificial synapse. A proprioceptive sensitivity is controlled using $V_2$>0 V. The negative feedback gradually limits potentiation of the EPSC of the artificial synapse according to the applied $V_2$.

An artificial efferent nerve has to have excitatory and inhibitory synaptic responses simultaneously to prevent muscle hyperextension, similar to the biological stretch reflex. Therefore, proprioceptive feedback is required to effectively limit excitatory synaptic responses and consequent muscle contractions in real time. In the presence of feedback, the operation of living organs is stable, but in the absence of feedback, the operation may be unstable due to excessive deformation.

The artificial proprioceptor device 10 forms a closed feedback loop together with the artificial synapse 20. An artificial proprioceptive feedback loop is based on a voltage divider with one or more resistors $R_1$ and $R_2$ and one or more voltage sources $V_1$ and $V_2$. This simple passive circuit produces an output voltage that is linearly dependent on a resistor in series with a voltage source to which an amplitude is applied. Since the voltage source $V_1$ takes an input from the action potential AP and is an alternating current (AC) signal, a resulting output voltage $V_{out}$ is also an AC signal.

Referring to FIG. 5, the applied voltage $V_1$ is adjusted to the output voltage $V_{out}$ through a ratio ($R_2/(R_1+R_2)$) between the resistance $R_1$ of the strain sensor constituting the voltage divider and $R_2$, which is the reference resistance, and the reference voltage $V_2$.

$$V_{out} = V_2 + (V_1 - V_2)\frac{R_2}{R_1 + R_2}$$

The output voltage $V_{out}$ is then transmitted to the artificial synapse 20, and when the resistance $R_1$ of the strain sensor 11 increases and the output voltage $V_{out}$ decreases, the post-synaptic output signal of the artificial synapse 20 becomes smaller, and thus, excessive muscle contraction may be controlled.

Next, a fabricating method for the low-power stretchable neuromorphic nerve device in accordance with the present disclosure will be described.

The strain sensor 10 forms a SEBS thin film on a substrate such as glass. The surface of the SEBS thin film is covered with a hollow-patterned film shadow mask and treated with oxygen plasma, thereby producing a uncovered hydrophilic surface. After removing the mask, a CNT strain sensor may be fabricated by dropping a single-walled CNT solution onto the hydrophilic pattern using a micropipette and drying it at room temperature.

(a) of FIG. 4 is a view illustrating a fabricating process of the artificial synapse 20 of the low-power stretchable neuromorphic nerve device in accordance with the present disclosure. Referring to (a) of FIG. 4, a gate electrode, a source electrode, and a drain electrode are formed on a substrate, and the substrate on which each electrode is formed is pre-strained, and then a semiconducting structure is formed to connect the source electrode and the drain electrode. The pre-strained substrate is released and an ion gel dielectric layer is formed between the source electrode and the drain electrode.

In accordance with the present disclosure, the artificial synapse 20 includes a single organic semiconductor nanowire, an ion-gel gate dielectric, and interdigitated source and drain electrodes of an elastomeric substrate. Electrodes may be formed, for example, by spray coating, electrohydrodynamics drop-on-demand (EHD DOD) jet printing, drop casting, spin coating, dip coating, electron beam evaporation, thermal evaporation, printing, photolithography, soft lithography, sputtering, and the like.

The ionic gel dielectric layer can be applied using a photopatterning process. For example, in a photopatterning process, an ionic gel ink comprising a polymeric monomer having the property of being cured and gelled by UV light, an initiator, and an ionic liquid is applied to a substrate having a patterned semiconductor layer, and a patterned mask is placed on the resulting ionic gel layer and exposing it to UV light to obtain an ionic gel dielectric layer.

An organic semiconducting nanowire emulating the shape of the neuron is very flexible and stretchable (100% strain). An organic semiconducting nanowire may be fabricated by electrospinning and transferred to a pre-strained elastomeric substrate. An array of artificial synapses 20 with a high resolution of 30 pixels per inch may be fabricated by directly printing a highly aligned serpentine nanowire array on the substrate. The artificial synapse 20 may maintain stable electrical properties even after 1,000 repeated stretching from 0% to 100% strain and up to 100% strain in both parallel and perpendicular directions to the charge transport (nanowire) direction. Such nano-scale channel dimensions may enable low-energy operation of the neuromorphic nerve device in accordance with the present disclosure. In the high-resolution device, instead of transferring the nanowire to the pre-strained substrate, the highly-aligned serpentine nanowire array may be printed directly onto the substrate.

By printing an ink composition containing an organic semiconductor material and a polymer through electrospinning, two adjacent electrodes are connected with the semiconducting structure. The ink composition for electrospinning essentially includes nanowires and a polymer, and preferably may further include a solvent. For the polymer, all polymers that may be electrospun may be used: for example, at least one selected from polyvinylpyrrolidone (PVP), polyvinyl alcohol (PVA), polyethylene oxide (PEO), polystyrene (PS), polycaprolactone (PCL), polyacrylonitrile (PAN), polymethyl methacrylate (PMMA), polyimide (PI), polyvinylidene fluoride (PVDF), polyaniline (PANI), and stadiene-ethylene-butadiene-styrene (SEBS) block copolymers may be used, and preferably, the thadiene-ethylene-butadiene-styrene (SEBS) block copolymer substrate may be used.

For the solvent, water, an organic solvent, or the like may be used. For the organic solvent, dichloroethylene, trichloroethylene, chloroform, chlorobenzene, dichlorobenzene, dichloromethane, styrene, dimethylformamide, dimethyl sulfoxide, tetrahydrofuran, xylene, toluene, cyclohexene, 2-methoxyethanol, ethanolamine, acetonitrile, butyl alcohol, isopropyl alcohol, ethanol, methanol, acetone, or a mixture thereof may be used.

The artificial synapse 20 may be formed on a flexible and stretchable polymer substrate. A flexible and stretchable artificial synapse may be fabricated by using a material and a conductive material that are stable against mechanical deformation. The conductive material stable against mechanical deformation may include a material selected from the group consisting of a carbon nanomaterial, a metal nanomaterial, and a liquid metal.

For example, the substrate may be a transparent inorganic substrate selected from the group consisting of glass and quartz, or may be a flexible substrate selected from the group consisting of polyethylene terephthalate, polyethylene naphthalate, polyethylene sulfone, polycarbonate, polystyrene, polypropylene, polyester, polyimide, polyetheretherketone, polyetherimide, acrylic resin, polyacrylate, polyethersulfone, polydimethylsiloxane, polymethylphenylsiloxane, polydiphenylsiloxane, polysiloxane, polyurethane, a styrene-butadiene copolymer, a polystyrene copolymer, a ecoflexolefin maleimide copolymer, and norbornene-based resin.

EXAMPLE

Fabrication Example

Fabrication of Electrospun Organic Nanowires

By using a conjugated polymer based on fused thiophene diketopyrrolopyrrole (FT4-DPP) in chloroform, poly[(3,7-bis(heptadecyl) thieno[3,2-b]thieno[2',3':4,5]thieno[2,3-d]thiophene-5,5'-diyl)(2,5-bis(8-octyloctadecyl)-3,6-di(thiophen-2-yl)pyrrolo[3,4-c]pyrrole-1,4(2H,5H)-dione-5,5'-diyl)] (provided by Corning, number average molecular weight 33,000 g mol-1, polydispersity index=2), and high molecular weight polyethylene oxide (Aldrich, weight average molecular weight 400,000 g $mol^{-1}$, 7:3 w:w), electrospinning was performed (printing parameters: tip-substrate distance 15 cm, external voltage 3 kV, solution supply rate 1 μl/min). A single strand of electrospun organic nanowires (average diameter: 566±90 nm) was transferred to a pre-strained CNT electrode-patterned SEBS substrate at 100% strain.

Fabrication of Organic Stretchable Electronic Synapse

Inter-digitated CNT source-drain electrodes were fabricated by spray-coating single-walled CNTs on a hydrophobic $SiO_2$/Si substrate and then transferred to a free-standing SEBS substrate (500 μm). A single electrospun organic semiconductor nanowire was placed on a 100% pre-strained CNT pattern SEBS substrate. When strain was released, the highly flexible nanowire maintained a stable wavy structure even after repeated mechanical deformation. A poly(styrene-b-methyl methacrylate-b-styrene) (PS-PMMA-PS)triblock copolymer and an ionic liquid dissolved in 1-ethyl-3-methylimidazolium bis(trifluoromethylsulfonyl)imide ([EMIM][TFSI]) ethyl acetate (0.7:9.3:90, w/w) were formed in a channel region by drop casting.

For the stability test in the PBS solution, instead of the PS-PMMA-PS triblock copolymer, poly(vinylidene fluoride-hexafluoropropylene) was used as a matrix material for the polymer gel electrolyte and encapsulated with polydimethylsiloxane to improve device stability.

Fabrication of Soft Electrode

Poly(3,4-ethylenedioxythiophene):poly(styrene sulfonate) (PEDOT:PSS) (Orgacon ICP 1050) was provided by Agfa as a surfactant-free aqueous dispersion with a solid content of 1.1% by weight. Prior to use, the PEDOT:PSS dispersion was filtered through a 1.0 μm filter to remove large clumps. Glycerol (G9012-100ML) was purchased from Sigma-Aldrich. 0.165 g of glycerol was added to 15 ml of PEDOT:PSS solution. The mixture was stirred vigorously at room temperature for 20 minutes. Then, the PEDOT:PSS/glycerol aqueous mixture was filtered through a 0.45-μm syringe filter. A SEBS solution (0.1 g $ml^{-1}$ in toluene) was drop cast onto a glass slide and left to dry overnight. After the solvent evaporated, the SEBS film was treated with oxygen plasma (Technics Micro-RIE Series 800, 150 W, 200 mTorr) for one minute. The prepared PEDOT:PSS/glycerol aqueous mixture was spin-coated on the SEBS film at 1,500 rpm and then annealed at 120° C. for ten minutes. A polyethylene terephthalate mask (cut into a 2 mm*40 mm rectangular pattern using Silution Cameo Cutter) was placed on the PEDOT:PSS/glycerol film and dry etched with oxygen plasma for ten minutes. Another SEBS film was stacked to the PEDOT:PSS/glycerol/SEBS film to encapsulate an interconnect area. The flexible electrode was annealed on a hot plate at 120° C. for 40 min. Electrodes were soaked in 1×PBS for at least two hours prior to in vivo application.

Fabrication of CNT Strain Sensor Using Self-Pinning Effect

A thin SEBS substrate (to 100 μm) was prepared on glass. The surface of the SEBS was covered with a hollow-patterned film shadow mask. The uncovered surface was made hydrophilic by treatment with oxygen plasma (150 W, 20 sec). After removing the mask, a CNT strain sensor was obtained by dropping a single-walled CNT solution onto the hydrophilic pattern using a micropipette and drying it at room temperature.

In Vivo Experiment

Animal Preparation

An adult (25 to 35 g) male C57BL/6J mice (Jackson Laboratories) were group-housed, where the mice received food pellets and water ad libitum, and a 12 hour:12 hour light/dark cycle was maintained. All animals were housed in a facility next to the laboratory starting 1 week before surgery and throughout post-surgery and behavioral analysis to minimize stress due to traffic and walking. All procedures were approved by Stanford University's Animal Care and Use Committee (protocol APLAC-31893) and Seoul National University's Institutional Animal Care and Committee (protocol SNU-201105-3) and were in accordance with the guidelines of the National Institutes of Health and Korea Food and Drug Administration. For in vivo electrical stimulation of muscles, mice were acclimated to the housing facility for at least one week and then anesthetized using isoflurane or ketamine/xylazine or alpaxane/xylazine. A heating pad at 37° C. was placed under the main body. To ensure that the animal was fully anesthetized, the hindpaw was pinched with tweezers to confirm the absence of the paw reflex and the absence of the eye reflex. Then, both legs were shaved from knee to hip using an electric razor. Eye protection liquid gel was applied to the eyes with a cotton swab. The surgical site was then wiped with a gauze pad or cotton swab and disinfected with chlorhexidine and 70% ethanol. The depth of anesthesia was monitored by periodically pinching the paws of the mice.

A 2 cm incision was made in the skin to expose the rectus femoris and gastrocnemius. Soft and elastic hydrogel electrodes (surface area 8 $mm^2$) or needle electrodes (25G) were gently connected to extensor and flexor muscles. After implantation, the skin was sutured with a surgical knot. Electrodes were connected to the artificial proprioceptor device and the artificial synapse. A pre-synaptic gate voltage pulse was applied to the artificial synapse. Extracellular recording data were collected by Matthew G. Perich in the laboratory of Lee E. Miller at Northwestern University and downloaded from CRCNS.org.

Biomimetic input action potential (AP) signals were applied to the artificial proprioceptor device and then transmitted to the artificial synapse. Single unit APs in the data set were recorded from neurons in the premotor cortex using a multi-electrode array. Leg responses were recorded using a digital microscope. Force generated by leg motion was measured with a force gauge placed next to the mouse leg. Protractor marks printed on paper were placed under the leg to enable measurement of a swing angle. Electromyography was used to record muscle activity during electrical stimulation. Three needle electrodes were used to penetrate the muscle and the electrodes were connected to a signal acquisition system (Muscle SpikerBox, Backyard Brain). To demonstrate natural movements such as kicking, walking, and running, the mouse was suspended on a vertical supporter on the ground.

SNEN and Electrophysiological Signals

In addition, to demonstrate applicability of the SNEN to future neuromorphic neurorehabilitation devices, neural signals that has been recorded from the animal's primary motor cortex during limb movements in advance were used as pre-synaptic input signals to artificial efferent neurons. Electrophysiological data of two single-unit recorded neurons were sampled from a public data set. The firing patterns of the two neurons were used as a gate voltage for the artificial synapse. Neuron 1 with a high firing rate (34.8 Hz) evoked higher EPSC amplitudes than Neuron 2 with a low firing rate (2.8 Hz).

This device is capable of processing electrical input of multiple neurons. The electrophysiological data of seven single-unit recorded neurons (numbers 1 to 7) were extracted from the public data set ((a) and (b) of FIG. 10). Two pre-synaptic input signal patterns consisting of combined signals from five neurons (numbers 1 to 5) were projected to SNEN A, and combined signals from five neurons (numbers 3 to 7) were projected to SNEN B ((c) of FIG. 10). SNEN A is connected to the flexor muscle and SNEN B is connected to the extensor muscle ((c) of FIG. 5). As an analogue of an axon, this device calculated the output EPSC by summing several neural inputs at different firing rates ((d) and (e) of FIG. 10). Then, the muscles were activated by a voltage signal converted from the EPSC by an I/V converter. During the entire process, the SNEN received nerve signals from the motor cortex and initiated movement in the muscles by bypassing the spinal cord and a peripheral nervous system. Two muscles were alternately stimulated and different angular swing motions were executed ((f) of FIG. 10). Since the SNEN may trigger muscle movement by relaying single-unit electrophysiological signals to muscles, the possibility of controlling limb movements by receiving nerve signals from the brain using a simple device consisting of a single strain sensor and an artificial synapse was confirmed.

Muscle Activation Device Measurement Using SNEN Artificial Synapse

A pre-synaptic voltage spike was applied to the gate electrode ($V_G$=−1 V) and a post-synaptic current was read from the drain electrode ($V_D$=−1 V) with a source electrode grounded.

Neuromorphic Nerve Device (SNEN)

A pre-synaptic voltage spike was applied to the gate electrode ($V_G$=−1 V) and a source voltage of 1 V. For muscle stimulation, an output signal was amplified by connecting the drain electrode to the I/V converter.

To quantify how muscle contraction is affected by a frequency $f_{AP}$ of AP, a single artificial synapse was connected to the knee flexor of an anesthetized mouse hind limb (FIG. 2). EMG signals induced electrophysiological activity of muscles. As $f_{AP}$ increased from 1 Hz to 11 Hz, the maximum angular displacement increased from 6.67° to 40° ((b) to (e) of FIG. 7). An isometric force of the mouse hind limb was measured by stimulating the extensor AP at $1 \le f_{AP} \le 50$ Hz ((f) of FIG. 7). The maximum force increased from 39 mN to 412 mN (4 g to 42 g) as $f_{AP}$ increased ((g) of FIG. 7). This change occurred because the muscle contraction response changed from a weak contraction at low $f_{AP}$ to continuous and strong contraction at high $f_{AP}$. The gradually increased muscle force response and smooth leg motion were achieved by the artificial synapse in response to post-synaptic signal potentiation. This response is clearly different from the abrupt increase then decrease in muscle force and drastic leg motion induced by stimulation using electrical pulses of constant amplitude in the related art. To emulate synchronized movement, two artificial synapses, one to a flexor and the other to an extensor ((h) of FIG. 7). APs at $f_{AP}$=50 Hz were applied alternately to the artificial synapses at intervals of 1 second, and each muscle was stimulated to extend and flex in sequence ((i) to (k) of FIG. 7). Soft and stretchable electrically conductive hydrogel electrodes were used as a bio-interface to the muscles. A nanoporous conductive polymer network gave high electrochemical surface area and low impedance of 0.5 kΩ at $f_{AP}$=1 kHz. The hydrogel electrode (electrode area 8 $mm^2$) elicited higher angular displacement of the leg than did needle electrodes (25G, electrode area 10 $mm^2$) ((i) and (j) of FIG. 7).

Bipedal Walking with SNEN

The feasibility of using the SNEN in practical locomotion was shown with a mouse suspended by a vertical supporter ((a) of FIG. 9). Input signals were applied to the artificial synapse that was connected to an extensor of the right hind leg. Input signal patterns were regulated to control the swing motion of the leg. The EPSC signals were sufficient to elicit a sharp contraction of the extensor, so the leg could swing fully and kick a ball to a greater distance than hind leg length.

Bipedal walking locomotion was implemented ((b) of FIG. 9). One artificial synapse was connected to the flexor in the left leg and the extensor in the right leg, while the other transistor was connected to the extensor in the left leg and the flexor in the right leg ((c) of FIG. 9). Alternating input signals to each SNEN induced bipedal walking locomotion ((d) of FIG. 9). By adjusting the input APs, the moving speed from slow walking (0.8 cm $s^{-1}$) to running (2.5 cm $s^{-1}$) on a treadmill was controlled ((e) to (g) of FIG. 9). These results suggest that the SNEN has the potential to provide locomotion in living animals.

Artificial Proprioceptor Device and Power Consumption Analysis

Proprioception is required for basic motor functions such as standing and walking. The absence of proprioceptive feedback degrades the locomotion and damages muscles, thereby impairing interactions between neuroprosthetics users and the physical environment. Therefore, restoring motor functions with proprioception in patients with neurological disorders has long been the goal in medicine and bioengineering. However, development of methods to achieve proprioceptive feedback in neurorehabilitation devices is still a challenge. An artificial muscle spindle-based proprioceptive feedback loop could provide unconditioned proprioceptive feedback to temporal-spatial coordination of limb movement, and prevent damage of muscle caused by overstraining.

It was confirmed that the artificial proprioceptor device detects leg movement and prevents overstretching of the muscle ((a) and (b) of FIG. 7). The artificial proprioceptor device formed a closed feedback loop together with the artificial synapse ((c) of FIG. 7). A sensor composed of CNTs was used to mimic the biological muscle spindle and to detect the extension of the leg. The sensitive CNT strain sensor was fabricated using a capillary-flow-based self-pinning effect. The sensor has a resistance range from 100 kΩ to 3 MΩ in the strain sensing range from 0% to 50%, and is capable of operating with low hysteresis ((d) and (e) of FIG. 7).

Simulation of power calculation of an array of the SNEN system demonstrated that its power consumption (6.1 mW) is two orders of magnitude lower than a system composed of a one-transistor/one-strain sensor array connected to silicon integrated circuit chips with a microprocessor (928 mW) (FIG. 12). The reduction of power consumption occurs because the SNEN system operates only in response to events whereas the silicon integrated circuit chips with a microprocessor operate continuously.

Long-Term Stability Test

The long-term stability test of SEBS-encapsulated CNT strain sensors and soft hydrogel electrodes in phosphate-buffered saline (PBS, 1×, pH 7.4) solution was performed (FIG. 13). An aging time $T_{AA}$ was accelerated by increasing the temperature of the PBS solution at 60° C., which is 23° C. above body temperature TBT.

For stability testing of the artificial synapse in the PBS solution, instead of poly(styrene-b-methyl methacrylate-b-styrene)triblock copolymer (PS-PMMA-PS), poly(vinylidenefluoride-hexafluoro propylene) (PVDF-HFP) was used as the matrix material of the polymer gel electrolyte and encapsulated with PDMS to improve the stability of the device.

Artificial synapses with PVDF-HFP matrices showed synaptic responses similar to devices with PS-PMMA-PS matrices (FIG. 13). A maximum on-current and threshold voltage Vth of the artificial synapse were stably maintained for six days at 60° C., corresponding to 30 days in TBT 37° C. with an aging factor Q10=2 (FIG. 13). The stability of the artificial synapse was additionally measured for 14 days under ambient conditions, and as a result, it showed uniform I-V characteristics.

The above-described low-power stretchable neuromorphic nerve device in accordance with the present disclosure may be implemented with a hardware component, a software component, and/or a combination of a hardware component and a software component. For example, the device and components described in the exemplary embodiments may be implemented by using one or more general purpose computers or special purpose computers, for example, like a processor, controller, arithmetic logic unit (ALU), digital signal processor, microcomputer, field programmable array (FPA), programmable logic unit (PLU), microprocessor, or any other device capable of executing and responding to instructions.

A low-power stretchable neuromorphic nerve device in accordance with various exemplary embodiments of the present disclosure is a soft neural interface and flexible electronic system capable of bypassing electrophysiological signal paths damaged by spinal cord injury or motor neuron disease and redirecting electrophysiological signals to control or restore body movement.

A neuromorphic nerve device in accordance with an exemplary embodiment of the present disclosure can drive an ion gel dielectric-based organic artificial synapse with low voltage, and the artificial synapse can be driven with low power because the artificial synapse forms a small nanowire channel with a width of hundreds of nanometers and can be driven with low power because the artificial synapse operates on an event basis, that is, by receiving only signals generated in a channel to which a stimulation (an event) is given.

Synaptic signal potentiation of the neuromorphic system in accordance with the present disclosure essentially exhibits electrical signal ramping, which, in principle, can improve natural movement and patient comfort without the use of bulky additional electronic components such as a function generator (or functional electrical stimulator).

A stretchable neuromorphic prosthetic device (or prosthesis) in accordance with an exemplary embodiment of the present disclosure can be advantageously used for rehabilitation or treatment of patients with spinal cord injury, stroke, multiple sclerosis, motor neuron disease, and traumatic brain injury. A neuromorphic nerve device in accordance with the present disclosure has excellent stretchability, so that a robot made of a soft material similar to a human or an animal can be made, and a neuromorphic prosthetic device that is comfortable for a user to wear can be made possible.

The present disclosure has been described in detail with specific exemplary embodiments above, but the descriptions are merely illustrative, and it could be understood by those skilled in the art to which the present disclosure that various modifications and variations are possible from the above descriptions. Therefore, the scope of the present disclosure should be construed as defined by the following claims, and their equivalents.

What is claimed is:

1. A neuromorphic nerve device comprising:

an artificial proprioceptor device comprising:

at least one sensor configured to detect an external stimulus, a nerve stimulus, a body movement, or a biometric signal and to generate an electrical signal corresponding thereto; and a passive circuit configured to produce an output voltage that is dependent on the electrical signal of the at least one sensor;

an artificial synapse comprising a semiconducting structure and a plurality of electrodes, wherein the artificial synapse is configured to process electrical input signals received from the artificial proprioceptor device and to generate a corresponding post-synaptic signal for delivery to a biological motor organ; and one or more bio-interface electrodes electrically coupled to the artificial synapse and configured to transmit the post-synaptic signal to the biological motor organ, wherein the artificial proprioceptor device and the artificial synapse form a closed feedback loop system such that the at least one sensor of the artificial proprioceptor device detects deformation or movement of the biological motor organ or a physiological signal associated therewith.

2. The neuromorphic nerve device of claim 1, wherein the closed feedback loop system is a closed negative feedback loop or a closed positive feedback loop.

3. The neuromorphic nerve device of claim 1, wherein the artificial proprioceptor device emulates a muscle spindle or a golgi tendon organ.

4. The neuromorphic nerve device of claim 1, wherein the at least one sensor comprises: one or more sensors selected from the group consisting of a strain sensor for detecting muscle length and force, a pressure sensor, an optical sensor, an image sensor for detecting visual information, an acceleration sensor for detecting balance, and a gyroscope sensor.

5. The neuromorphic nerve device of claim 4, wherein the pressure sensor comprises a sensor configured to detect external light, pressure, tactile sensation, friction, sound, vibration, or heat and to convert a detected result into an electrical signal.

6. The neuromorphic nerve device of claim 4, wherein the strain sensor is one or more selected from the group consisting of a piezoresistive strain sensor, a piezoelectric strain sensor, a triboelectric strain sensor, and a capacitive strain sensor that change electrical signals by changing resistance, current, voltage, and permittivity according to strain or change optical characteristics by changing light transmittance and light absorption.

7. The neuromorphic nerve device of claim 6, wherein the strain sensor includes one or more conductive or semiconducting materials selected from the group consisting of carbon nanotubes, carbon nanofibers, carbon black, graphene, a transition metal dichalcogenide, MXene, graphene oxide, an inorganic semiconductor membrane, metal film crack sensors, metal nanowires, metal nanoparticles, conjugated polymers, metal oxide nanoparticles, metal oxide thin films, metal oxide nanowires, and semiconducting nanowires.

8. The neuromorphic nerve device of claim 4, wherein the pressure sensor is one or more selected from the group consisting of a piezoresistive pressure sensor, a piezoelectric pressure sensor, a triboelectric pressure sensor, and a capacitive pressure sensor that change electrical signals by changing resistance, current, voltage, and permittivity according to pressure or change optical characteristics by changing light transmittance and light absorption.

9. The neuromorphic nerve device of claim 1, wherein the passive circuit comprises a voltage divider.

10. The neuromorphic nerve device of claim 9, wherein the voltage divider comprises one or more resistors and one or more voltage sources.

11. The neuromorphic nerve device of claim 1, wherein the artificial synapse includes:

an active material; and one or more selected from the group consisting of a transistor with two or more terminal electrodes, a diode, a resistor, a capacitor, an inductor, an ion pump, and an ion battery structure, and the active material includes one or more selected from the group consisting of an organic small molecule semiconductor, an organic polymer semiconductor, a conductive polymer, an insulating polymer, a metal oxide material, a phase change alloy material, a carbon nanomaterial, a nitride material, a two-dimensional layered material, a material having a perovskite structure, a metal nanomaterial, an ionic dielectric material, and a mixture thereof.

12. The neuromorphic nerve device of claim 11, wherein the transistor includes:

a semiconducting structure that forms a channel region; and an ion gel dielectric layer that forms a dielectric layer between the channel region and the gate electrode.

13. The neuromorphic nerve device of claim 12, wherein the semiconducting structure is an organic semiconducting structure based on an organic material and includes an organic small molecule semiconductor, an organic polymer semiconductor, a conductive polymer, an insulating polymer, or a mixture thereof, the organic small molecule semiconductor is a small molecule material having a conjugated structure and having a band gap of 0.1 eV or more and less than 6.0 eV, and the organic polymer semiconductor is a polymer material having a conjugated structure and having a band gap of 0.1 eV or more and less than 6.0 eV, and the insulating polymer is a polymer material having a band gap of 6.0 eV or more or insulating properties.

14. The neuromorphic nerve device of claim 13, wherein the organic semiconducting structure is one or more selected from the group consisting of a thin film, nanoparticles, nanowires, nanofibers, nanofibrils, nanowhiskers, nanorods, nanotubes, and nanobelts.

15. The neuromorphic nerve device of claim 12, wherein, instead of the organic semiconducting structure, as an active material, the semiconducting structure is one or more selected from the group consisting of a metal oxide material, a phase change alloy material, a carbon nanomaterial, a nitride material, a two-dimensional layered material, a material having a perovskite structure, a metal nanomaterial, nanoparticles, quantum dots, plate-like particles, nanowires, an ionic dielectric material, and a mixture thereof.

16. The neuromorphic nerve device of claim 1, wherein the artificial synapse has a stretchability ranging from 1% to 10,000%.

17. The neuromorphic nerve device of claim 1, wherein the artificial synapse includes a substrate, and the substrate includes at least one selected from the group consisting of flexible and stretchable, flexible, and stretchable substrate materials.

18. The neuromorphic nerve device of claim 1, wherein the artificial synapse uses an active material and a conductive electrode material that are stable against mechanical deformation.

19. The neuromorphic nerve device of claim 1, wherein the one or more bio-interface electrodes comprise a hydrogel electrode that is connected to the artificial synapse and applies a post-synaptic current to the biological motor organ.

20. The neuromorphic nerve device of claim 19, wherein the hydrogel includes one or more selected from the group consisting of fibrin gel, collagen, agarose gel, matrigel, puramatrix, poly vinyl alcohol (PVA), poly(ethylene glycol) methacrylate (PEGMA), poly(ethylene glycol) diacrylate (PEGDA), alginate, 2-hydroxyethyl methacrylate (HEMA), polyacrylic acid, polyacrylamide gel, and a mixture thereof.

21. The neuromorphic nerve device of claim 19, wherein the hydrogel includes one or more selected from the group consisting of polyaniline, polypyrrole, poly(3,4-ethylenedioxythiophene) (PEDOT), a carbon nanomaterial, a metal nanomaterial, an ionic dielectric material, and a mixture thereof as a conductive filler.

22. The neuromorphic nerve device of claim 1, further comprising a resistor and an amplifier, wherein the amplifier is a current-to-voltage amplifier that amplifies a post-synaptic current.

23. A low-power neuromorphic prosthetic device comprising:

the neuromorphic nerve device of claim 1; and a controller configured to remotely control operation of the neuromorphic nerve device.

* * * * *